(12) United States Patent
Vianello et al.

(10) Patent No.: US 6,794,385 B2
(45) Date of Patent: Sep. 21, 2004

(54) BENZOXAZINE DERIVATIVES USEFUL AS INTEGRIN RECEPTOR ANTAGONISTS

(75) Inventors: Paola Vianello, Milan (IT); Tiziano Bandiera, Gambolò (IT); Mario Varasi, Milan (IT)

(73) Assignee: Pharmacia & Upjohn, S.p.A., Milan (IT)

( * ) Notice: Subject to any disclaimer, the term of this patent is extended or adjusted under 35 U.S.C. 154(b) by 0 days.

(21) Appl. No.: 09/924,732

(22) Filed: Aug. 8, 2001

(65) Prior Publication Data
US 2003/0069236 A1 Apr. 10, 2003

(51) Int. Cl.[7] .................. A61K 31/538; C07D 165/36
(52) U.S. Cl. ..................................... 514/230.5; 544/105
(58) Field of Search ........................ 544/105; 514/230.5

(56) References Cited
FOREIGN PATENT DOCUMENTS

| WO | 9950257 | 10/1999 |
|----|---------|---------|
| WO | 0039103 | 7/2000 |
| WO | 0069827 | 11/2000 |

Primary Examiner—Richard L. Raymond
(74) Attorney, Agent, or Firm—Rachel A. Polster; Harness Dickey & Pierce, P.L.C.

(57) ABSTRACT

The present invention relates to a class of compounds represented by the formula (I)

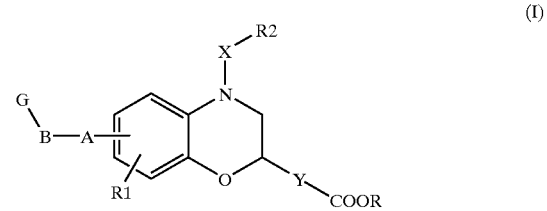

or a pharmaceutical acceptable salt, prodrug or ester thereof, pharmaceutical compositions comprising compounds of the formula (I), and methods of selectively inhibiting or antagonizing $\alpha_v\beta_3$ integrin.

27 Claims, No Drawings

BENZOXAZINE DERIVATIVES USEFUL AS INTEGRIN RECEPTOR ANTAGONISTS

FIELD OF THE INVENTION

The present invention relates to novel compounds which bind to the integrin receptor $\alpha_v\beta_3$, to pharmaceutical compositions containing such compounds, processes for preparing such compounds, and to methods of using these compounds, alone or in combination with other therapeutic agents.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked $\alpha$ and $\beta$ polypeptide subunits. Currently eleven different $\alpha$ subunits have been identified and six different $\beta$ subunits have been identified. The various $\alpha$ subunits can combine with various $\beta$ subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis, Paget's disease, humoral hypercalcemia of malignancy, angiogenesis, including tumor angiogenesis, retinopathy including macular degeneration, arthritis, including rheumatoid arthritis, periodontal disease, psoriasis and smooth muscle cell migration (e.g. restenosis artherosclerosis). Additionally, it has been found that such agents would be useful as antivirals, antifungals and antimicrobials. Thus, compounds which selectively inhibit or antagonize $\alpha_v\beta_3$ would be beneficial for treating such conditions.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

The compounds of this invention are therefore selective $\alpha_v\beta_3$ integrin antagonists. The present invention includes compounds which inhibit the respective integrin and also includes pharmaceutical compositions comprising such compounds. The present invention further provides for methods for treating or preventing conditions mediated by the $\alpha_v\beta_3$ receptor in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. U.S.A., Vol. 89 (1992) 1557–1561) have shown that the $\alpha_v\beta_3$ integrin has a biological function in melanoma cell invasion. Montgomery et al., (Proc. Natl. Acad. Sci. U.S.A., Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy including macular degeneration (Adamis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic agents for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (loss of bone), which leads to an increased number of bone fractures, incapacitation and increased mortality. Antagonists of $\alpha_v\beta_3$ have been shown to be potent inhibitors of osteoclastic activity both in vitro [Sato et al., J. Cell. Biol., Vol. 111 (1990) 1713–1723] and in vivo [Fisher et al., Endocrinology, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc. Surg. Vol. 19(1) (1994) 125–34). Prevention or inhibition of neointimal hyperplasia by pharmaceutical agents to prevent or inhibit restenosis would be beneficial.

White (Current Biology, Vol. 3(9)(1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

SUMMARY OF THE INVENTION

The present invention as a first object provides compounds of the following formula (I)

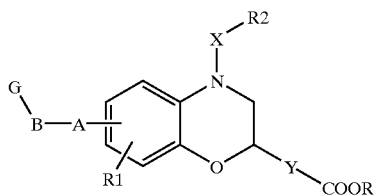

(I)

or a pharmaceutically acceptable salt, prodrug or ester thereof, wherein

G is selected from the group consisting of:

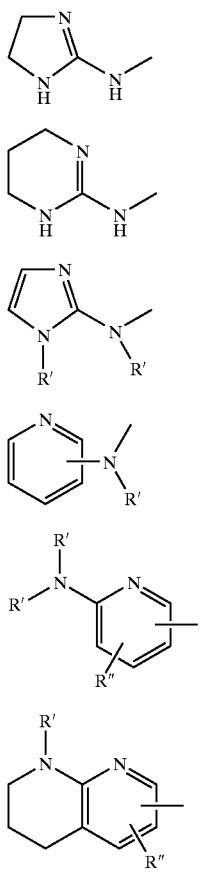

a)

wherein Q is NH or O and Q' is H, $C_1$-$C_6$ alkyl, phenyl, or phenyl-$C_1$-$C_4$-alkyl;

b)

c)

d)

e)

f)

g)

wherein R' and R" are independently H or $C_1$-$C_4$ alkyl;
B is a $C_1$-$C_4$ alkyl or a $C_2$-$C_4$ alkenyl;
A is $CH_2$, O, S(O)$_n$ wherein n is zero, 1 or 2, NH, a group CON(R''') or N(R''')CO wherein R''' is hydrogen or $CH_3$;

R1 is selected from the group consisting of H, $C_1$-$C_4$ alkyl, $C_1$-$C_4$ alkoxy, OH, halogen, and $CF_3$;

X is C=O or completes a single bond;

R2 is selected from the group consisting of H, $C_1$-$C_4$ alkyl, $C_3$-$C_7$ cycloalkyl, $C_1$-$C_4$-alkylcycloalkyl; aryl unsubstituted or optionally substituted by one to three substituents independently selected from halogen, $CF_3$, $C_1$-$C_4$ alkyl, hydroxy and $C_1$-$C_4$ alkoxy; aralkyl; and $C_5$-$C_7$ monocyclic heteroaryl ring containing one to three heteroatoms chosen from O, S, and N, unsubstituted or optionally substituted by one to three substituents independently selected from halogen, $CF_3$, $C_1$-$C_4$ alkyl, hydroxy and $C_1$-$C_4$ alkoxy;

Y is $(CH_2)_n$ wherein n is 1 or 2;

R is hydrogen, $C_1$-$C_6$ alkyl, $C_2$-$C_4$ alkenyl, $C_2$-$C_4$ alkynyl, aryl or aryl-$C_1$-$C_4$ alkyl.

With the proviso that m can not be 0 when G is:

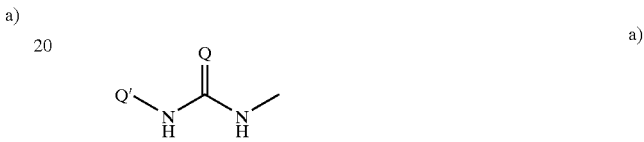

a)

wherein Q' is H and Q is O and X is $(C=O)_m$.

The present invention includes within its scope all possible isomers, stereoisomers and optical isomers and their mixtures, and the bioprecursors or metabolites of the compounds of formula (I).

It is another object of the invention to provide pharmaceutical compositions comprising compounds of the Formula I. Such compounds and compositions are useful in selectively inhibiting or antagonizing the $\alpha_v\beta_3$ integrin and therefore in another embodiment the present invention relates to a method of selectively inhibiting or antagonizing the $\alpha_v\beta_3$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

DETAILED DESCRIPTION

The present invention relates to a class of compounds represented by the Formula I, described above.

A halogen atom is preferably chlorine or fluorine.

The alkyl, alkoxy, alkenyl and alkynyl groups and the alkylene and alkenylene chains may be branched or straight groups or chains, respectively.

A $C_3$-$C_7$ cycloalkyl group is, e.g., a cyclopropyl, cyclobutyl, cyclopentyl, cyclohexyl or cycloheptyl group, in particular cyclopropyl, cyclopentyl and cyclohexyl.

A $C_1$-$C_4$ alkylcyclopropyl group is a $C_1$-$C_4$ alkyl group linked to a $C_3$-$C_7$ cycloalkyl group, such as, for instance, cyclopropylmethyl, cyclobutylmethyl, cyclopentylmethyl, cyclohexylmethyl, cyclopentylethyl, cyclohexylethyl and the like.

An aryl group is, e.g., an aromatic $C_6$-$C_{20}$ mono- or polynuclear moiety, typically phenyl or naphthyl.

A $C_5$-$C_7$ monocyclic heteroaryl ring as defined above is preferably a $C_5$-$C_6$ heteromonocyclic ring, in particular selected from pyridine, pyrazine, pyridazine, pyrimidine, thiophene, pyrrole, pyrazole, imidazole, oxazole and isoxazole.

An aralkyl group is e.g. benzyl or phenethyl, in which the phenyl ring is optionally substituted by one to three substituents independently chosen from halogen, hydroxy, $CF_3$, $C_1$–$C_4$ alkyl and $C_1$–$C_4$ alkoxy.

A $C_2$–$C_4$ alkenyl group is preferably an allyl group.

A $C_1$–$C_6$ alkyl group is preferably a $C_1$–$C_4$ alkyl group.

A $C_1$–$C_4$ alkyl group is preferably a methyl or ethyl group.

A $C_2$–$C_4$ alkynyl group is preferably an ethynyl group.

A $C_1$–$C_4$ alkoxy group is preferably methoxy, ethoxy, propoxy and butoxy.

Examples of pharmaceutically acceptable salts of the compounds of the invention are those with either inorganic bases, such as sodium, potassium, calcium and aluminum hydroxides, or organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic acids, e.g. hydrochloric, hydrobromic, sulphuric and phosphoric acids and with organic acids, e.g. citric, tartaric, maleic, malic, fumaric, trifluoroacetic, methanesulphonic and ethanesulphonic acids. As stated above, the present invention also includes within its scope pharmaceutically acceptable bio-precursors (otherwise known as pro-drugs) of the compounds of formula (I), i.e. compounds which have a different formula to formula (I) above, but which nevertheless upon administration to a human being are converted directly or indirectly in vivo into a compound of formula (I).

A further object of the present invention is to provide a compound of formula (I), as herein defined, or a pharmaceutically acceptable salt thereof, for use in a method of treatment of the human or animal body by therapy, in particular for treating conditions mediated by the $\alpha_v\beta_3$ integrin.

The object of the present invention is also to provide a pharmaceutical composition comprising a pharmaceutically acceptable carrier and/or diluent and as an active principle a compound of formula (I), as herein defined, or a pharmaceutically acceptable salt thereof.

The present invention also provides the use of a compound of formula (I), as defined above, in the preparation of a medicament having $\alpha_v\beta_3$ integrin inhibiting or antagonizing activity.

The present invention also provides a method for treating conditions mediated by the $\alpha_v\beta_3$ integrin in a mammal, including humans, in need of such treatment comprising administering to said mammal an effective $\alpha_v\beta_3$ inhibiting or antagonizing amount of a compound of formula (I)

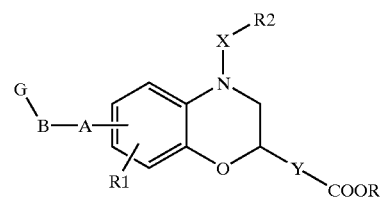

(I)

or a pharmaceutically acceptable salt, prodrug or ester thereof, wherein:

G is selected from the group consisting of

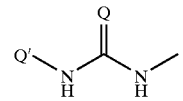

a)

wherein Q is NH or O and Q' is H, $C_1$–$C_6$ alkyl, phenyl, or phenyl-$C_1$–$C_4$-alkyl;

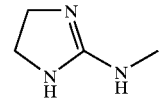

b)

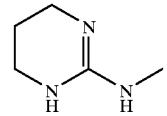

c)

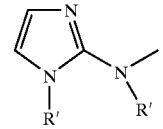

d)

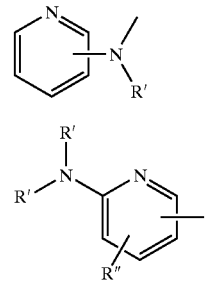

e)

f)

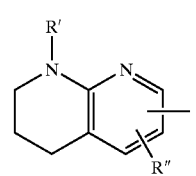

g)

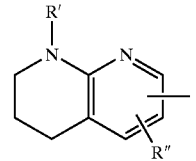

wherein R' and R" are independently H or $C_1$–$C_4$alkyl;

B is a $C_1$–$C_4$ alkyl or a $C_2$–$C_4$ alkenyl;

A is $CH_2$, O, $S(O)_n$ wherein n is zero, 1 or 2, NH, a group CON(R''') or N(R''')CO wherein R''' is hydrogen or $CH_3$;

R1 is selected from the group consisting of H, $C_1$–$C_4$ alkyl, $C_1$–$C_4$ alkoxy, OH, halogen, and $CF_3$;

X is C=O or completes a single bond;

R2 is selected from the group consisting of H, $C_1$–$C_4$ alkyl, $C_3$–$C_7$ cycloalkyl, $C_1$–$C_4$-alkylcycloalkyl; aryl unsubstituted or optionally substituted by one to three substituents independently selected from halogen, $CF_3$, $C_1$–$C_4$ alkyl, hydroxy and $C_1$–$C_4$ alkoxy; aralkyl; and $C_5$–$C_7$ monocyclic heteroaryl ring containing one to three heteroatoms selected from O, S, and N, unsubstituted or optionally substituted by one to three substituents independently selected from halogen, $CF_3$, $C_1$–$C_4$ alkyl, hydroxy and $C_1$–$C_4$ alkoxy;

Y is $(CH_2)_n$ wherein n is 1 or 2;

R is hydrogen, $C_1$–$C_6$ alkyl, $C_2$–$C_4$ alkenyl, $C_2$–$C_4$ alkynyl, aryl or aryl-$C_1$–$C_4$ alkyl.

With the proviso that m can not be 0 when G is:

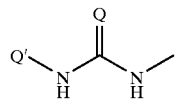

a)

wherein Q' is H and Q is O and X is $(C=O)_m$.

More specifically, the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, arthritis, psoriasis and periodontal disease, and inhibiting smooth muscle cell migration including restenosis.

Preferred compounds of the invention are those wherein, in formula (I), G is selected from the group consisting of

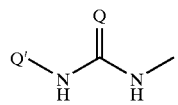

a)

wherein Q is NH or O and Q' is H, $C_1$–$C_6$ alkyl, phenyl, or phenyl-$C_1$–$C_4$-alkyl;

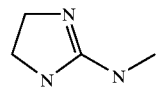

b)

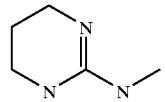

c)

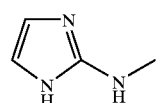

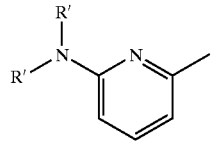

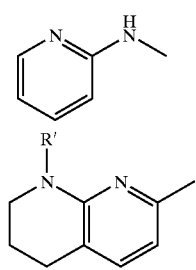

wherein R' is as defined above;
B, X, R, R1 and A are as defined above;
R2 is a phenyl, pyridine, pyrazine, pyridazine, pyrimidine, thiophene, pyrrole, pyrazole, imidazole, oxazole or isoxazole ring, unsubstituded or optionally substituted by one or two substituents selected from halogen, $CF_3$, $C_1$–$C_4$ alkyl, OH and $C_1$–$C_4$ alkoxy;

Y is $CH_2$.

With the proviso that m can not be 0 when G is:

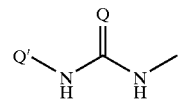

a)

wherein Q' is H and Q is O and X is $(C=O)_m$.

Most preferred compounds of the invention are those wherein, in formula (I), G is selected from the group consisting of

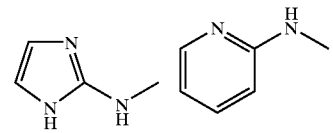

B, X, R, R1 and A are as defined above;
R2 is a phenyl or pyridine ring unsubstituted or optionally substituted by one or two substituents selected from halogen, $CF_3$, $C_1$–$C_4$ alkyl, OH and $C_1$–$C_4$ alkoxy;
Y is $CH_2$; and a pharmaceutically acceptable salts, prodrug or ester thereof.

Examples of specific preferred compounds according to the invention are the following:

(4-phenyl-6-{[3-(2-pyridinylamino)propanoyl]amino}-3,4-dihydro-2H-1,4-benzoxazin-2-yl)acetic acid;
(4-phenyl-6-{[4-(2-pyridinylamino)butanoyl]amino}-3,4-dihydro-2H-1,4-benzoxazin-2-yl)acetic acid;
(4-phenyl-6-{[5-(2-pyridinylamino)pentanoyl]amino}-3,4-dihydro-2H-1,4-benzoxazin-2-yl)acetic acid
(4-phenyl-6-{[3-(1H-imidazol-2-ylamino)propanoyl]amino}-3,4-dihydro-2H-1,4-benzoxazin-2-yl)acetic acid;
(4-phenyl-6-{[4-(1H-imidazol-2-ylamino)butanoyl]amino}-3,4-dihydro-2H-1,4-benzoxazin-2-yl)acetic acid;
(4-phenyl-6-{[5-(1H-imidazol-2-ylamino)pentanoyl]amino}-3,4-dihydro-2H-1,4-benzoxazin-2-yl)acetic acid;
(4-methyl-6-{[3-(2-pyridinylamino)propanoyl]amino}-3,4-dihydro-2H-1,4-benzoxazin-2-yl)acetic acid;
(4-methyl-6-{[4-(2-pyridinylamino)butanoyl]amino}-3,4-dihydro-2H-1,4-benzoxazin-2-yl)acetic acid;
(4-methyl-6-{[5-(2-pyridinylamino)pentanoyl]amino}-3,4-dihydro-2H-1,4-benzoxazin-2-yl)acetic acid;
(4-methyl-6-{[3-(1H-imidazol-2-ylamino)propanoyl]amino}-3,4-dihydro-2H-1,4-benzoxazin-2-yl)acetic acid;
(4-methyl-6-{[4-(1H-imidazol-2-ylamino)butanoyl]amino}-3,4-dihydro-2H-1,4-benzoxazin-2-yl)acetic acid;
(4-methyl-6-{[5-(1H-imidazol-2-ylamino)pentanoyl]amino}-3,4-dihydro-2H-1,4-benzoxazin-2-yl)acetic acid;
(4-cyclopropylmethyl-6-{[3-(2-pyridinylamino)propanoyl]amino}-3,4-dihydro-2H-1,4-benzoxazin-2-yl)acetic acid;
(4-cyclopropylmethyl-6-{[4-(2-pyridinylamino)butanoyl]amino}-3,4-dihydro-2H-1,4-benzoxazin-2-yl)acetic acid;
(4-cyclopropylmethyl-6-{[5-(2-pyridinylamino)pentanoyl]amino}-3,4-dihydro-2H-1,4-benzoxazin-2-yl)acetic acid;
(4-cyclopropylmethyl-6-{[3-(1H-imidazol-2-ylamino)propanoyl]amino}-3,4-dihydro-2H-1,4-benzoxazin-2-yl)acetic acid;
(4-cyclopropylmethyl-6-{[4-(1H-imidazol-2-ylamino)butanoyl]amino}-3,4-dihydro-2H-1,4-benzoxazin-2-yl)acetic acid;

(4-cyclopropylmethyl-6-{[5-(1H-imidazol-2-ylamino)
pentanoyl]amino}-3,4-dihydro-2H-1,4-benzoxazin-2-yl)
acetic acid;
(4-cyclohexylmethyl-6-{[3-(2-pyridinylamino)propanoyl]
amino}-3,4-dihydro-2H-1,4-benzoxazin-2-yl)acetic acid;
(4-cyclohexylmethyl-6-{[4-(2-pyridinylamino)butanoyl]
amino}-3,4-dihydro-2H-1,4-benzoxazin-2-yl)acetic acid;
(4-cyclohexylmethyl-6-{[5-(2-pyridinylamino)pentanoyl]
amino}-3,4-dihydro-2H-1,4-benzoxazin-2-yl)acetic acid;
(4-cyclohexylmethyl-6-{[3-(1H-imidazol-2-ylamino)
propanoyl]amino}-3,4-dihydro-2H-1,4-benzoxazin-2-yl)
acetic acid;
(4-cyclohexylmethyl-6-{[4-(1H-imidazol-2-ylamino)
butanoyl]amino}-3,4-dihydro -2H-1,4-benzoxazin-2-yl)
acetic acid;
(4-cyclohexylmethyl-6-{[5-(1H-imidazol-2-ylamino)
pentanoyl]amino}-3,4-dihydro-2H-1,4-benzoxazin-2-yl)
acetic acid;
(4-benzyl-6-{[3-(2-pyridinylamino)propanoyl]amino}-3,4-
dihydro-2H-1,4-benzoxazin-2-yl)acetic acid;
(4-benzyl-6-{[4-(2-pyridinylamino)butanoyl]amino}-3,4-
dihydro-2H-1,4-benzoxazin-2-yl)acetic acid;
(4-benzyl-6-{[5-(2-pyridinylamino)pentanoyl]amino}-3,4-
dihydro-2H-1,4-benzoxazin-2-yl)acetic acid;
(4-benzyl-6-{[3-(1H-imidazol-2-ylamino)propanoyl]
amino}-3,4-dihydro-2H-1,4-benzoxazin-2-yl)acetic acid;
(4-benzyl-6-{[4-(1H-imidazol-2-ylamino)butanoyl]amino}-
3,4-dihydro-2H-1,4-benzoxazin-2-yl)acetic acid;
(4-benzyl-6-{[5-(1H-imidazol-2-ylamino)pentanoyl]
amino}-3,4-dihydro-2H-1,4-benzoxazin-2-yl)acetic acid;
(4-benzoyl-6-{[3-(2-pyridinylamino)propanoyl]amino}-3,
4-dihydro-2H-1,4-benzoxazin-2-yl)acetic acid;
(4-benzoyl-6-{[4-(2-pyridinylamino)butanoyl]amino}-3,4-
dihydro-2H-1,4-benzoxazin-2-yl)acetic acid;
(4-benzoyl-6-{[5-(2-pyridinylamino)pentanoyl]amino}-3,4-
dihydro-2H-1,4-benzoxazin-2-yl)acetic acid;
(4-benzoyl-6-{[3-(1H-imidazol-2-ylamino)propanoyl]
amino}-3,4-dihydro-2H-1,4-benzoxazin-2-yl)acetic acid;
(4-benzoyl-6-{[4-(1H-imidazol-2-ylamino)butanoyl]
amino}-3,4-dihydro-2H-1,4-benzoxazin-2-yl)acetic acid;
(4-benzoyl-6-{[5-(1H-imidazol-2-ylamino)pentanoyl]
amino}-3,4-dihydro-2H-1,4-benzoxazin-2-yl)acetic acid;
(4-nicotinoyl-6-{[3-(2-pyridinylamino)propanoyl]amino}-
3,4-dihydro-2H-1,4-benzoxazin-2-yl)acetic acid;
(4-nicotinoyl-6-{[4-(2-pyridinylamino)butanoyl]amino}-3,
4-dihydro-2H-1,4-benzoxazin-2-yl)acetic acid;
(4-nicotinoyl-6-{[5-(2-pyridinylamino)pentanoyl]amino}-
3,4-dihydro-2H-1,4-benzoxazin-2-yl)acetic acid;
(4-nicotinoyl-6-{[3-(1H-imidazol-2-ylamino)propanoyl]
amino}-3,4-dihydro-2H-1,4-benzoxazin-2-yl)acetic acid;
(4-nicotinoyl-6-{[4-(1H-imidazol-2-ylamino)butanoyl]
amino}-3,4-dihydro-2H-1,4-benzoxazin-2-yl)acetic acid;
(4-nicotinoyl-6-{[5-(1H-imidazol-2-ylamino)pentanoyl]
amino}-3,4-dihydro-2H-1,4-benzoxazin-2-yl)acetic acid;
[4-phenyl-6-{[2-(2-pyridinylamino)ethylamino]carbonyl}-
3,4-dihydro-2H-1,4-benzoxazin-2-yl]acetic acid;
[4-phenyl-6-{[3-(2-pyridinylamino)propylamino]
carbonyl}-3,4-dihydro-2H-1,4-benzoxazin-2-yl]acetic
acid;
[4-phenyl-6-{[4-(2-pyridinylamino)butylamino]carbonyl}-
3,4-dihydro-2H-1,4-benzoxazin-2-yl]acetic acid;
[4-phenyl-6-{[2-(1H-imidazol-2-ylamino)ethylamino]
carbonyl}-3,4-dihydro-2H-1,4-benzoxazin-2-yl]acetic
acid;
[4-phenyl-6-{[3-(1H-imidazol-2-ylamino)propylamino]
carbonyl}-3,4-dihydro-2H-1,4-benzoxazin-2-yl]acetic
acid;
[4-phenyl-6-{[4-(1H-imidazol-2-ylamino)butylamino]
carbonyl}-3,4-dihydro-2H-1,4-benzoxazin-2-yl]acetic
acid.

A further object of the present invention is a combined method of treatment of cancer or of controlling the growth of the neoplasm in mammals, including humans, suffering from cancer, said method comprising administering 1) a compound of the invention, or a pharmaceutically acceptable salt thereof, and
2) an additional antitumor agent, in amounts and close enough together in time sufficient to produce a therapeutically useful effect.

The present invention also provides a product containing a compound of the invention, or a pharmaceutically acceptable salt thereof, and an effective antineoplastic amount of additional antitumor agent as a combined preparation for simultaneous, separate or sequential use in anti-cancer therapy.

The object of the present invention is to provide the use of a compound of formula (I), as herein defined, or a pharmaceutically acceptable salt thereof, in the manufacture of a medicament having $\alpha_v\beta_3$ integrin inhibiting or antagonizing activity for controlling the growth of the neoplasm in a patient undergoing a simultaneous, separate or sequential treatment with another antitumor agent.

The combination preparation according to the invention can also include combination packs or compositions in which the constituents are placed side by side and can therefore be administered simultaneously, separately or sequentially to one and the same human being. Accordingly, the antineoplastic agent and a compound according to the present invention may be present within a single or distinct container means.

In the combined preparations, pharmaceutical compositions and methods of treating, according to the present invention, the antineoplastic agent may comprise 1 to 4, preferably 1, 2 or 3, antineoplastic drugs, in particular a single antineoplastic drug.

As used herein, "controlling the growth" of the neoplasm refers to slowing, interrupting, arresting or stopping its growth and it does not necessarily indicate a total elimination of the neoplasm. It is believed that prolonging the survivability of a patient, beyond being a significant advantageous effect in and of itself, also indicates that the condition is beneficially controlled to some extent.

The term "antineoplastic agent" is meant to comprise both a single antineoplastic cytotoxic drug and "cocktails", i.e. mixtures of such drugs, according to the clinical practice.

As used herein, the term "effective antineoplastic amount" refers to an amount which is effective, upon single or multiple dose administration to the patient, in controlling the growth of the neoplasm or in prolonging the survivability of the patient beyond that expected in the absence of such treatment.

An antineoplastic agent, according to the invention, is preferably selected from the group comprising: an antineoplastic topoisomerase II inhibitor, an antineoplastic antimicrotubule agent, an antineoplastic alkylating agent, an antineoplastic antimetabolite and an antineoplastic topoisomerase I inhibitor.

An antineoplastic topoisomerase II inhibitor is preferably:
a) an anthracycline compound e.g. doxorubicin (including liposomal formulations) daunomycin, methoxy-morpholino-doxorubicin, epirubicin (including liposomal formulation), idarubicin and nemorubicin; and b) an anthraquinone compound e.g. mitoxantrone and losoxantrone; and
c) a podophillotoxine compound e.g. etoposide and teniposide.

An antimicrotubule agent is preferably:
a) a taxane compound e.g. paclitaxel (including liposomal formulations) and docetaxel; and
b) a vinca alkaloid e.g. vinblastine and vinorelbine.

An alkylating agent is preferably cyclophosphamide, ifosfamide, chlorambucil, melphalan and PNU 159548 (C. Geroni et al., Proc. Am. Assoc. Cancer Res 39, p223, 1998 (Abstr. #1517).

An antineoplastic antimetabolite agent is e.g. 5-fluorouracil, capecitabine, gemcitabine, methotrexate and edatrexate.

An antineoplastic topoisomerase I inhibitor is e.g. topotecan, irinotecan, 9-nitrocamptothecin and PNU 166148 (Compound A1 in WO 99/17804).

An antineoplastic agent is in particular epirubicin, doxorubicin, liposome-encapsulated doxorubicin, docetaxel, paclitaxel and liposome-encapsulated paclitaxel.

Particularly preferred preparations, pharmaceutical compositions and methods of treating, according to the present invention, are those comprising a) 1, 2 or 3 antineoplastic agents selected from epirubicin, doxorubicin, idarubicin, paclitaxel, docetaxel, 5-fluorouracil, cyclophosphamide and vinorelbine, and b) a compound of the invention or a pharmaceutically acceptable salt thereof.

The effective antineoplastic amounts of the various antineoplastic agents are well known and appreciated in the art.

For example, an effective antineoplastic amount of vinblastine may vary from about 3 mg/m$^2$ to about 10 mg/m$^2$.

An effective antineoplastic amount of doxorubicin may vary from about 20 mg/m$^2$ to about 100 mg/m$^2$.

An effective antineoplastic amount of epirubicin may vary from about 20 mg/m$^2$ to about 200 mg/m$^2$.

An effective antineoplastic amount of idarubicin may vary from about 1 mg/m$^2$ to about 50 mg/m$^2$.

An effective antineoplastic amount of mitoxantrone may vary from about 10 mg/m$^2$ to about 20 mg/m$^2$.

An effective antineoplastic amount of paclitaxel may vary from about 100 mg/m$^2$ to about 300 mg/m$^2$.

An effective antineoplastic amount of docetaxel may vary from about 50 mg/m$^2$ to about 100 mg/m$^2$.

An effective antineoplastic amount of vinorelbine may vary from about 15 mg/m$^2$ to about 30 mg/m$^2$.

An effective antineoplastic amount of cyclophosphamide may vary from about 100 mg/m$^2$ to about 1500 mg/m$^2$.

An effective antineoplastic amount of melphalan may vary from about 1 mg/m$^2$ to about 10 mg/m$^2$.

An effective antineoplastic amount of 5-fluorouracil may vary from about 100 mg/m$^2$ to about 1000 mg/m$^2$.

An effective antineoplastic amount of capecitabine may vary from about 10 mg/m$^2$ to about 1000 mg/m$^2$.

An effective antineoplastic amount of methotrexate may vary from about 10 mg/m$^2$ to about 1000 mg/m$^2$.

An effective antineoplastic amount of topotecan may vary from about 1 mg/m$^2$ to about 5 mg/m$^2$.

An effective antineoplastic amount of irinotecan may vary from about 50 mg/m$^2$ to about 350 mg/m$^2$.

In effecting treatment of a patient afflicted with a disease state described above a compound of formula (I) of the invention can be administered in any form or mode which makes the compound bioavailable in effective amounts, including oral and parenteral routes. For example, it can be administered orally, subcutaneously, intraperitoneally, intramuscularly, intravenously, transdermally, and the like.

Oral or intramuscular administration is generally preferred. One skilled in the art of preparing formulations can readily select the proper form and mode of administration depending upon the particular circumstances, including the disease state to be treated, the stage of the disease, the form of administration of the selected cytotoxic agent and the manner of co-administration selected.

The selected antineoplastic agent can be administered by the appropriate route and dosing schedule as is well known and accepted for the particular agent. For example, epirubicin, doxorubicin, idarubicin, paclitaxel, docetaxel, 5-fluorouracil, cyclophosphamide and vinblastine can be administered intravenously. Idarubicin and cyclophosphamide can also be given orally.

In the combined preparations, pharmaceutical compositions, method of treating and therapeutic uses, according to the present invention, speficic preferred compounds of the invention are the following:

(4-phenyl-6-{[3-(2-pyridinylamino)propanoyl]amino}-3,4-dihydro-2H-1,4-benzoxazin-2-yl)acetic acid;
(4-phenyl-6-{[4-(2-pyridinylamino)butanoyl]amino}-3,4-dihydro-2H-1,4-benzoxazin-2-yl)acetic acid;
(4-phenyl-6-{[5-(2-pyridinylamino)pentanoyl]amino}-3,4-dihydro-2H-1,4-benzoxazin-2-yl)acetic acid;
(4-phenyl-6-{[3-(1H-imidazol-2-ylamino)propanoyl]amino}-3,4-dihydro-2H-1,4-benzoxazin-2-yl)acetic acid;
(4-phenyl-6-{[4-(1H-imidazol-2-ylamino)butanoyl]amino}-3,4-dihydro-2H-1,4-benzoxazin-2-yl)acetic acid;
(4-phenyl-6-{[5-(1H-imidazol-2-ylamino)pentanoyl]amino}-3,4-dihydro-2H-1,4-benzoxazin-2-yl)acetic acid;
(4-methyl-6-{[3-(2-pyridinylamino)propanoyl]amino}-3,4-dihydro-2H-1,4-benzoxazin-2-yl)acetic acid;
(4-methyl-6-{[4-(2-pyridinylamino)butanoyl]amino}-3,4-dihydro-2H-1,4-benzoxazin-2-yl)acetic acid;
(4-methyl-6-{[5-(2-pyridinylamino)pentanoyl]amino}-3,4-dihydro-2H-1,4-benzoxazin-2-yl)acetic acid;
(4-methyl-6-{[3-(1H-imidazol-2-ylamino)propanoyl]amino}-3,4-dihydro-2H-1,4-benzoxazin-2-yl)acetic acid;
(4-methyl-6-{[4-(1H-imidazol-2-ylamino)butanoyl]amino}-3,4-dihydro-2H-1,4-benzoxazin-2-yl)acetic acid;
(4-methyl-6-{[5-(1H-imidazol-2-ylamino)pentanoyl]amino}-3,4-dihydro-2H-1,4-benzoxazin-2-yl)acetic acid;
(4-cyclopropylmethyl-6-{[3-(2-pyridinylamino)propanoyl]amino}-3,4-dihydro-2H-1,4-benzoxazin-2-yl)acetic acid;
(4-cyclopropylmethyl-6-{[4-(2-pyridinylamino)butanoyl]amino}-3,4-dihydro-2H-1,4-benzoxazin-2-yl)acetic acid;
(4-cyclopropylmethyl-6-{[5-(2-pyridinylamino)pentanoyl]amino}-3,4-dihydro-2H-1,4-benzoxazin-2-yl)acetic acid;
(4-cyclopropylmethyl-6-{[3-(1H-imidazol-2-ylamino)propanoyl]amino}-3,4-dihydro-2H-1,4-benzoxazin-2-yl)acetic acid;
(4-cyclopropylmethyl-6-{[4-(1H-imidazol-2-ylamino)butanoyl]amino}-3,4-dihydro -2H-1,4-benzoxazin-2-yl)acetic acid;
(4-cyclopropylmethyl-6-{[5-(1H-imidazol-2-ylamino)pentanoyl]amino}-3,4-dihydro-2H-1,4-benzoxazin-2-yl)acetic acid;
(4-cyclohexylmethyl-6-{[3-(2-pyridinylamino)propanoyl]amino}-3,4-dihydro-2H-1,4-benzoxazin-2-yl)acetic acid;
(4-cyclohexylmethyl-6-{[4-(2-pyridinylamino)butanoyl]amino}-3,4-dihydro-2H-1,4-benzoxazin-2-yl)acetic acid;
(4-cyclohexylmethyl-6-{[5-(2-pyridinylamino)pentanoyl]amino}-3,4-dihydro-2H-1,4-benzoxazin-2-yl)acetic acid;
(4-cyclohexylmethyl-6-{[3-(1H-imidazol-2-ylamino)propanoyl]amino}-3,4-dihydro-2H-1,4-benzoxazin-2-yl)acetic acid;

(4-cyclohexylmethyl-6-{[4-(1H-imidazol-2-ylamino) butanoyl]amino}-3,4-dihydro -2H-1,4-benzoxazin-2-yl) acetic acid;
(4-cyclohexylmethyl-6-{[5-(1H-imidazol-2-ylamino) pentanoyl]amino}-3,4-dihydro-2H-1,4-benzoxazin-2-yl) acetic acid;
(4-benzyl-6-{[3-(2-pyridinylamino)propanoyl]amino}-3,4-dihydro-2H-1,4-benzoxazin-2-yl)acetic acid;
(4-benzyl-6-{[4-(2-pyridinylamino)butanoyl]amino}-3,4-dihydro-2H-1,4-benzoxazin-2-yl)acetic acid;
(4-benzyl-6-{[5-(2-pyridinylamino)pentanoyl]amino}-3,4-dihydro-2H-1,4-benzoxazin-2-yl)acetic acid;
(4-benzyl-6-{[3-(1H-imidazol-2-ylamino)propanoyl] amino}-3,4-dihydro-2H-1,4-benzoxazin-2-yl)acetic acid;
(4-benzyl-6-{[4-(1H-imidazol-2-ylamino)butanoyl]amino}-3,4-dihydro-2H-1,4-benzoxazin-2-yl)acetic acid;
(4-benzyl-6-{[5-(1H-imidazol-2-ylamino)pentanoyl] amino}-3,4-dihydro-2H-1,4-benzoxazin-2-yl)acetic acid;
(4-benzoyl-6-{[3-(2-pyridinylamino)propanoyl]amino}-3,4-dihydro-2H-1,4-benzoxazin-2-yl)acetic acid;
(4-benzoyl-6-{[4-(2-pyridinylamino)butanoyl]amino}-3,4-dihydro-2H-1,4-benzoxazin-2-yl)acetic acid;
(4-benzoyl-6-{[5-(2-pyridinylamino)pentanoyl]amino}-3,4-dihydro-2H-1,4-benzoxazin-2-yl)acetic acid;
(4-benzoyl-6-{[3-(1H-imidazol-2-ylamino)propanoyl] amino}-3,4-dihydro-2H-1,4-benzoxazin-2-yl)acetic acid;
(4-benzoyl-6-{[4-(1H-imidazol-2-ylamino)butanoyl] amino}-3,4-dihydro-2H-1,4-benzoxazin-2-yl)acetic acid;
(4-benzoyl-6-{[5-(1H-imidazol-2-ylamino)pentanoyl] amino}-3,4-dihydro-2H-1,4-benzoxazin-2-yl)acetic acid;
(4-nicotinoyl-6-{[3-(2-pyridinylamino)propanoyl]amino}-3,4-dihydro-2H-1,4-benzoxazin-2-yl)acetic acid;
(4-nicotinoyl-6-{[4-(2-pyridinylamino)butanoyl]amino}-3,4-dihydro-2H-1,4-benzoxazin-2-yl)acetic acid;
(4-nicotinoyl-6-{[5-(2-pyridinylamino)pentanoyl]amino}-3,4-dihydro-2H-1,4-benzoxazin-2-yl)acetic acid;
(4-nicotinoyl-6-{[3-(1H-imidazol-2-ylamino)propanoyl] amino}-3,4-dihydro-2H-1,4-benzoxazin-2-yl)acetic acid;
(4-nicotinoyl-6-{[4-(1H-imidazol-2-ylamino)butanoyl] amino}-3,4-dihydro-2H-1,4-benzoxazin-2-yl)acetic acid;
(4-nicotinoyl-6-{[5-(1H-imidazol-2-ylamino)pentanoyl] amino}-3,4-dihydro-2H-1,4-benzoxazin-2-yl)acetic acid;
[4-phenyl-6-{[2-(2-pyridinylamino)ethylamino]carbonyl}-3,4-dihydro-2H-1,4-benzoxazin-2-yl]acetic acid;
[4-phenyl-6-{[3-(2-pyridinylamino)propylamino] carbonyl}-3,4-dihydro-2H-1,4-benzoxazin-2-yl]acetic acid;
[4-phenyl-6-{[4-(2-pyridinylamino)butylamino]carbonyl}-3,4-dihydro-2H-1,4-benzoxazin-2-yl]acetic acid;
[4-phenyl-6-{[2-(1H-imidazol-2-ylamino)ethylamino] carbonyl}-3,4-dihydro-2H-1,4-benzoxazin-2-yl]acetic acid;
[4-phenyl-6-{[3-(1H-imidazol-2-ylamino)propylamino] carbonyl}-3,4-dihydro-2H-1,4-benzoxazin-2-yl]acetic acid;
[4-phenyl-6-{[4-(1H-imidazol-2-ylamino)butylamino] carbonyl}-3,4-dihydro-2H-1,4-benzoxazin-2-yl]acetic acid;

The compounds of the invention and the salt thereof can be prepared by and in analogy to the following processes.

A compound of formula (I) wherein A, B, X, Y, R, R1 and R2 are as defined above, and G is as defined under d) to g), can be obtained by reacting a compound of formula (II)

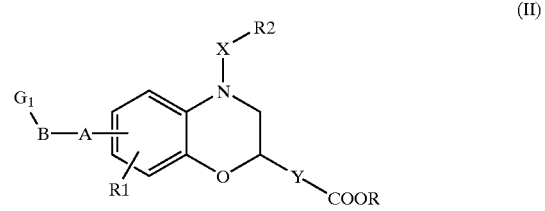

wherein A, B, X, Y, R, R1 and R2 are as defined above, and $G_1$ is represented by G, as defined above under d) to g) wherein one or more nitrogens are protected with suitable protective groups, such as, for instance, carbobenzyloxy or t-butoxycarbonyl, removable with a suitable reducing agent, or with an acid, such as trifluoroacetic acid or hydrochloric or hydrobromic acid.

A compound of formula (II) can be obtained by:

1) reacting a compound of formula (III)

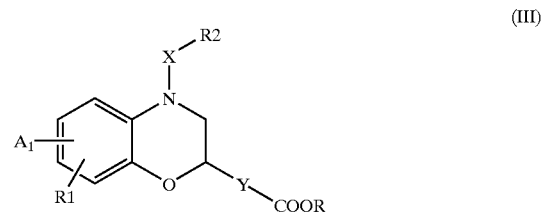

wherein X, Y, R, R1 and R2 are as defined above, and $A_1$ is NH(R'''), wherein R''' is as defined above, with a compound of formula (IV)

$G_1$—B—COOH    (IV)

wherein $G_1$ and B are as defined above, in the presence of a suitable condensing agent such as, for instance, N,N'-dicyclohexylcarbodiimide, N,N'-diisopropylcarbodiimide, 1-ethyl-3-(3-dimethylaminopropyl)carbodiimide, O-(benzotriazol-1-yl)-N,N,N',N'-tetramethyluronium tetrafluoborate, Mukayama's reagent or other condensing agents known to those skilled in the art, thus obtaining a compound of formula (II) wherein $G_1$, B, X, Y, R, R1 and R2 are as defined above, and A is N(R''')CO; or 2) reacting a compound of formula (III), wherein X, Y, R, R1 and R2 are as defined above, and $A_1$ is OH, with a compound of formula (V)

$G_1$—B—W    (V)

wherein $G_1$ and B are as defined above, and W is Cl, Br, I, OH, $OSO_2C_1$–$C_4$-alkyl or $OSO_2$Aryl, thus obtaining a compound of formula (II) wherein $G_1$, B, X, Y, R, R1 and R2 are as defined above, and A is O; or 3) reacting a compound of formula (III), wherein X, Y, R, R1 and R2 are as defined above, and $A_1$ is SH, with a compound of formula (V), wherein $G_1$ and B are as defined above and W is different from OH, thus obtaining a compound of formula (II) wherein $G_1$, B, X, Y, R, R1 and R2 are as defined above, and A is S; or 4) reacting a compound of formula (III), wherein X, Y, R, R1 and R2 are as defined above, and $A_1$ is NH(R'''), with a compound of formula V, wherein $G_1$, and B are as defined above and W is different from OH, thus obtaining a compound of formula (II) wherein $G_1$, B, X, Y, R, R1 and R2 are as defined above, and A is N(R'''); or 5) reacting a compound of formula (VI)

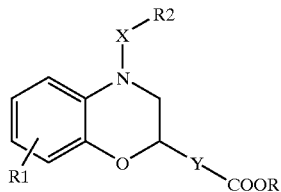

(VI)

wherein X, Y, R, R1 and R2 are as defined above, with a compound of formula (IV), as defined above, using a suitable condensing agent such as, for instance, polyphosphoric acid or ethyl polyphosphate or trifluoroacetic anhydride or trifluoromethanesulfonic acid or other agents known to those skilled in the art, followed by treatment of the resulting product with a reducing agent such as hydrogen in presence of a suitable metal catalyst, such as palladium on carbon, or triethylsilane in trifluoroacetic acid, thus obtaining a compound of formula (II) wherein $G_1$, B, X, Y, R, R1 and R2 are as defined above, and A is $CH_2$; or 6) reacting a compound of formula (VII)

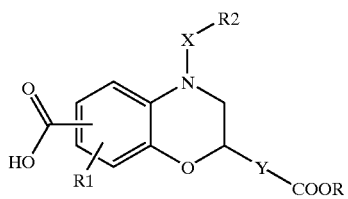

(VII)

wherein X, Y, R, R1 and R2 are as defined above, with a compound of formula (VIII)

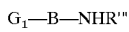 (VIII)

wherein $G_1$, B and R''' are as defined above, in the presence of suitable condensing agents such as those described under 1), thus obtaining a compound of formula (II) wherein $G_1$, B, X, Y, R, R1 and R2 are as defined above, and A is CON(R''').

7) reacting a compound of formula (II), wherein $G_1$, B, X, Y, R, R1 and R2 are as defined above, and A is S, with a suitable oxydizing agent, such as $NaIO_4$, oxone, $H_2O_2$ or a peracid, thus obtaining a compound of formula (II) wherein $G_1$, B, X, Y, R, R1 and R2 are as defined above, and A is S(O)n wherein n is 1 or 2, i.e. A is a sulfoxide or a sulfone group.

A compound of formula (I) wherein A, B, X, Y, R, R1 and R2 are as defined above, and G is as defined under b), c) or under a), wherein Q is different from oxygen, can be obtained by reacting a compound of formula (IX)

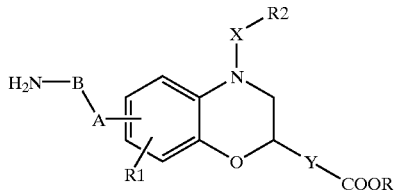

(IX)

wherein A, B, X, Y, R, R1 and R2 are as defined above, with a suitable guanilating agent such as, for example, N,N'-di-t-butoxycarbonyl-N''-triflylguanidine or 2-methylthio-2-imidazoline hydriodide or 2-methylthio-1,4,5,6-tetrahydropyrimidine hydriodide, followed by removal of the protecting groups in the case where the guanilating agent is N,N'-di-t-butoxycarbonyl-N''-triflylguanidine.

A compound of formula (I) wherein A, B, X, Y, R, R1 and R2 are as defined above, and G is as defined under a), wherein Q is oxygen, can be obtained by reacting a compound of formula (IX), as defined above, with an inorganic cyanate, such as sodium or potassium or ammonium cyanate, or with an isocyanate of formula Q'NCO, wherein Q' is as described above.

A compound of formula (IX,) in turn, can be obtained in analogy to the processes described under 1) to 6) by:

8) reacting a compound of formula (III)

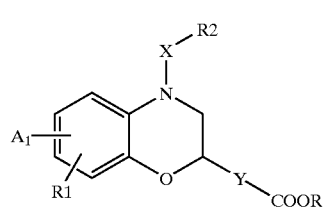

(III)

where X, Y, R, R1 and R2 are as defined above, and $A_1$ is NH(R'''), wherein R''' is as defined above, with a compound of formula (X)

$Z_1$NH—B—COOH (X)

wherein B is as defined above and $Z_1$ is a suitable amino protecting group such as, for instance, benzyloxycarbonyl, tert-butoxycarbonyl or other protecting groups listed in GREENE, T. W., WUTS, P. G. M. Protective group in organic synthesis, Wiley, 1999, followed by removal of the amino protecting group, thus obtaining a compound of formula (IX) wherein B, X, Y, R, R1 and R2 are as defined above, and A is N(R''')CO; or, 9) reacting a compound of formula (III), wherein X, Y, R, R1 and R2 are as defined above, and $A_1$ is OH, with a compound of formula (XI)

$Z_1$NH—B—W (XI)

wherein B, W and $Z_1$ are as defined above, followed by removal of the amino protecting group, thus obtaining a compound of formula (IX) wherein B, X, Y, R, R1 and R2 are as defined above, and A is O; or 10) reacting a compound of formula (III), wherein X, Y, R, R1 and R2 are as defined above, and $A_1$ is SH, with a compound of formula (XI), wherein $Z_1$ and B are as defined above and W is different from OH, followed by removal of the amino protecting group, thus obtaining a compound of formula (IX) wherein B, X, Y, R, R1 and R2 are as defined above, and A is S; or 11) reacting a compound of formula (III), wherein X, Y, R, R1 and R2 are as defined above, and $A_1$ is SH, with a compound of formula (XI), wherein $Z_1$ and B are as defined above and W is different from OH, followed by treatment with a suitable oxydizing agent, such as oxone, $NaIO_4$, $H_2O_2$ or a peracid and subsequent removal of the amino protecting group, thus obtaining a compound of formula (IX) wherein B, X, Y, R, R1 and R2 are as defined above, and A is S(O)n wherein n is 1 or 2; or 12) reacting a compound of formula (III), wherein X, Y, R, R1 and R2 are as defined above, and $A_1$ is NH(R'''), with a compound of formula (XI), wherein $Z_1$ and B are as defined above and W is different from OH, followed by removal of the amino protecting group, thus obtaining a compound of formula (IX) wherein B, X, Y, R, R1 and R2 are as defined above, and A is N(R'''); or 13) reacting a compound of formula (VI)

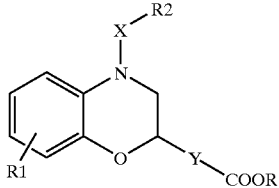

(VI)

wherein X, Y, R, R1 and R2 are as defined above, with a compound of formula (X), as defined above, in the presence of a suitable condensing agent such as those described under 5), followed by treatment of the resulting product with a reducing agent such as triethylsilane in trifluoroacetic acid, and removal of the amino protecting group thus obtaining a compound of formula (IX) wherein B, X, Y, R, R1 and R2 are as defined above, and A is $CH_2$; or 14) reacting a compound of formula (VII)

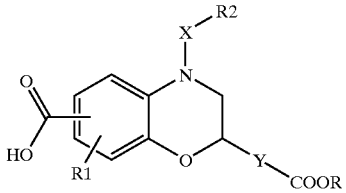

(VII)

wherein X, Y, R, R1 and R2 are as defined above, with a compound of formula (VIII)

$Z_1NH-B-NHR'''$  (XII)

wherein $Z_1$, B and R''' are as defined above, in the presence of a suitable condensing agent such as those described under 1), followed by removal of the amino protecting group, thus obtaining a compound of formula (IX) wherein B, X, Y, R, R1 and R2 are as defined above, and A is CON(R''').

The compounds of formula (III), (VI), and (VII) can be prepared from the properly substituted o-aminophenol, according to general synthetic methods for the preparation of 1,4-benzoxazines.

Additionally, a compound of formula (I) can be obtained by a process which comprises:

i) converting a compound of formula (I) into another compound of formula (I), or separating a single isomer of a compound of formula (I) from a mixture thereof, or converting a compound of formula (I) into a salt thereof, or converting a salt of a compound of formula (I) into a free compound of formula (I);

ii) reacting a compound of formula I wherein G, A, B, X, Y, R1 and R2 are as defined above and R is different from hydrogen with aqueous acids or aqueous bases thus obtaining a compound of formula I wherein R is hydrogen;

In particular, the compounds described above can be prepared as exemplified in the following procedures.

In a typical procedure, a compound of formula I, as defined above, can be obtained by treatment of a compound of formula II, as defined above, with hydrogen in the presence of a suitable catalyst, such as palladium on carbon, in a solvent like a lower alcohol or dioxane, or by treatment with trifluoroacetic acid or hydrobromic acid in acetic acid, followed by isolation of the product by chromatography.

In a typical procedure for the preparation of a compound of formula II, as described above, to a solution of a compound of formula III, wherein X, Y, R, R1 and R2 are as defined above, and $A_1$ is NH(R'''), wherein R''' is as defined above, and a compound of formula IV, as defined above, in a solvent like dichloromethane, tetrahydrofuran, dioxane or dimethylformamide are added 4-dimethylaminopyridine and a suitable condensing agent, such as N,N'-dicyclohexylcarbodiimide or N,N'-diisopropylcarbodiimide or 1-ethyl-3-(3-dimethylaminopropyl)carbodiimide or O-(benzotriazol-1-yl)-N,N,N',N'-tetramethyluronium tetrafluoborate or Mukayama's reagent. The reaction mixture is stirred at a temperature from about 0° C. to room temperature for 2 to 18 hours. The product is then isolated by column chromatography, thus obtaining a compound of formula II, wherein $G_1$, B, X, Y, R, R1 and R2 are as defined above, and A is N(R''')CO.

In a typical procedure for the preparation of a compound of formula II, as described above, to a solution of a compound of formula III, wherein X, Y, R, R1 and R2 are as defined above, and $A_1$ is OH, triphenylphosphine and a compound of formula V, as defined above and wherein W is OH, in a solvent like toluene or tetrahydrofuran or dichloromethane, a solution of an alkyl azodicarboxylate in toluene or tetrahydrofuran or dichloromethane is added and the mixture stirred at a temperature from room temperature to about 40° C. for 1 to 6 hours. The product is then isolated by column chromatography, thus obtaining a compound of formula II, wherein $G_1$, B, X, Y, R, R1 and R2 are as defined above, and A is O.

In a typical procedure for the preparation of a compound of formula II, as described above, a solution of a compound of formula II, wherein X, Y, R, R1 and R2 are as defined above, and $A_1$ is SH, in a solvent like tetrahydrofuran, acetone, dimethylformamide or dimethylsulfoxide or a lower alcohol, is treated with an organic or an inorganic base such as, for instance, triethylamine or potassium or sodium carbonate or potassium or sodium hydroxide, or sodium hydride, then a compound of formula V, as described above and wherein W is different from OH, is added. The reaction mixture is stirred at a temperature from room temperature to about 40° C. for 1 to 8 hours. The product is then isolated by column chromatography, thus obtaining a compound of formula II, wherein $G_1$, B, X, Y, R, R1 and R2 are as defined above, and A is S.

In a typical procedure for the preparation of a compound of formula II, as described above, to a solution of a compound of formula III, wherein X, Y, R, R1 and R2 are as defined above, and $A_1$ is NH(R'''), and an organic or an inorganic base such as, for instance, triethylamine or diisopropylethylamine or potassium or sodium carbonate, in a solvent like tetrahydrofuran, acetone, dimethylformamide or dimethylsulfoxide or a lower alcohol, a compound of formula V, as described above and wherein W is different from OH, is added. The reaction mixture is stirred at a temperature from room temperature to about 40° C. for 1 to 8 hours. The product is then isolated by column chromatography, thus obtaining a compound of formula II, wherein $G_1$, B, X, Y, R, R1 and R2 are as defined above, and A is N(R''').

In a typical procedure for the preparation of a compound of formula II, as defined above, a compound of formula VI, wherein X, Y, R, R1 and R2 are as defined above, and a compound of formula IV, as defined above, are mixed with polyphosphoric acid or ethyl polyphosphate or trifluoroacetic anhydride or trifluoromethanesulfonic acid and the mixture is stirred at a temperature from room temperature to 140° C., for 1 to 6 hours. The reaction is stopped by pouring into water, the product is extracted with a solvent like ethyl acetate or dichloromethane and the product is isolated by column chromatography. The product is then reduced by treatment with hydrogen in the presence of palladium on carbon, in a solvent like dioxane or a lower alcohol, thus obtaining a compound of formula II, wherein $G_1$, B, X, Y, R, R1 and R2 are as defined above, and A is $CH_2$.

In a typical procedure for the preparation of a compound of formula II, as defined above, to a solution of a compound of formula VII, wherein X, Y, R, R1 and R2 are as defined above, and a compound of formula VIII, as defined above, in a solvent like dichloromethane, tetrahydrofuran, dioxane or dimethylformamide are added 4-dimethylaminopyridine followed by a suitable condensing agent, such as N,N'-dicyclohexylcarbodiimide or N,N'-diisopropylcarbodiimide or 1-ethyl-3-(3-dimethylaminopropyl)carbodiimide or O-(benzotriazol-1-yl)-N,N,N',N'-tetramethyluronium tetrafluoborate or Mukayama's reagent. The reaction mixture is stirred at a temperature from about 0° C. to room temperature and for 2 to 18 hours. The product is then isolated by column chromatography, thus obtaining a compound of formula II, wherein $G_1$, B, X, Y, R, R1 and R2 are as defined above, and A is CON(R''').

In a typical procedure for the preparation of a compound of formula II, a compound of formula II, wherein $G_1$, B, X, Y, R, R1 and R2 are as defined above, and A is S, is treated with 30% aqueous $H_2O_2$ in a lower alcohol as a solvent, or with a peracid or with dimethyldioxirane, at a temperature from room temperature to about 50° C. for 1 to 6 hours. The product is then isolated by column chromatography, thus obtaining a compound of formula II, wherein $G_1$, B, X, Y, R, R1 and R2 are as defined above, and A is $SO_2$.

In a typical procedure for the preparation of a compound of formula II, a compound of formula II, wherein $G_1$, B, X, Y, R, R1 and R2 are as defined above, and A is S, is treated with $NaIO_4$ in water and methanol, or acetone and water, or with oxone in a mixture of methanol and water as a solvent, at a temperature from about −30° C. to room temperature for 1 to 4 hours. The product is then isolated by column chromatography, thus obtaining a compound of formula II, wherein $G_1$, B, X, Y, R, R1 and R2 are as defined above, and A is SO.

In a typical procedure for the preparation of a compound of formula I, wherein A, B, X, Y, R, R1, R2 are as defined above, and G is as defined under b), c) or under a) wherein Q is different from oxygen and Q' is hydrogen, a compound of formula IX, as defined above, is reacted with a suitable guanylating agent, like N,N'-di-t-butoxycarbonyl-N''-triflylguanidine or 2-methylthio-2-imidazoline hydriodide or 2-methylthio-1,4,5,6-tetrahydropyrimidine hydriodid in a solvent like dichloromethane, tetrahydrofuran, dioxane or a lower alcohol, at a temperature from room temperature to reflux, for 24 to 72 hours. The solvent is then evaporated and the residue is treated with trifluoroacetic acid when the reaction is performed with N,N'-di-t-butoxycarbonyl-N''-triflyl-guanidine. The product is then isolated by chromatography.

In typical procedure for the preparation of a compound of formula I, wherein A, B, X, Y, R, R1, R2 are as defined above, and G is as defined under a) wherein Q is oxygen and Q' is hydrogen, a compound of formula IX, as defined above, is reacted with a cyanate salt, as e.g. an ammonium or sodium or potassium salt, in a solvent such as acetic acid or water, at a temperature from about 50° C. to about 100° C., for 2 to 12 hours. The product is isolated by extraction or by filtration and is then purified by column chromatography.

In typical procedure for the preparation of a compound of formula I, wherein A, B, X, Y, R, R1, R2 are as defined above, and G is as defined under a) wherein Q is oxygen and Q' is different from hydrogen, a compound of formula IX, as defined above, is reacted with an isocyanate of formula Q'NCO, wherein Q' is as defined above, in a solvent like dichloromethane, acetonitrile, tetrahydrofuran, dioxane or toluene, in the presence of triethylamine, at a temperature from room temperature to about 100° C. and for 4 to 24 hours. The resulting compound is isolated by column chromatography. The preparation of a compound of formula IX, as described above, can be performed according to the processes described under 8) to 14) and applying the procedures described above.

The preparation of 1,4-benzoxazines III, VI, and VII from the properly substituted o-aminophenol can be carried out following known procedures as described, for instance, in METHODS OF ORGANIC CHEMISTRY (HOUBEN-WEIL), volume E 9a, pp. 141–177, George Thieme Verlag, Stuttgart 1997, or by suitable modifications of such methods as known to those skilled in the art.

Additionally, in a typical procedure, a compound of formula I, as defined above and wherein R is hydrogen, is obtained by treatment of a compound of formula I, as defined above and wherein R is different form hydrogen, with a mixture of an aqueous acid, like hydrochloric acid, and a lower alcohol or dioxane, at a temperature from room temperature to about 40° C., for 1 to 24 hours. Alternatively, a compound of formula I, as defined above and wherein R is different form hydrogen, is treated with an aqueous base, like sodium or lithium or potassium hydroxide, in a solvent like methanol or ethanol or dioxane, at a temperature from room temperature to about 40° C., for 1 to 24 hours. The solution is then treated with an acid and the compound filtered.

The optional salification of a compound of formula I as well as the conversion of a salt into the free compound and the separation of a mixture of isomers into the single isomers may be carried our by conventional methods. For example, the separation of optical isomers can be carried out by salification with an optically active base or acid and by subsequent fractional crystallisation of the diastereoisomeric salts, followed by recovering of the optically active isomeric acids or bases, respectively.

The compounds of formula I and the pharmaceutically acceptable salts thereof are herein defined as the "compounds of the present invention", the "compounds of the invention" and/or the "active principles of the pharmaceutical compositions of the invention".

Pharmacology

The compounds of the invention are selective integrin receptor inhibitors or antagonists, in particular they are inhibitors or antagonists of the $\alpha_v\beta_3$ integrin receptors. The specific inhibiting or antagonist activity of the compounds of the invention is shown for instance by the fact that they are active in in vitro solid phase $\alpha_v\beta_3$-vitronectin binding assay, as described below.

$\alpha_v\beta_3$-vitronectin Binding Assay

A solid phase assay for the study of $\alpha_v\beta_3$-vitronectin binding was set up on the basis of already published methods (Wong et al., Molecular Pharmacology 50: 529–537, 1996; Brooks et al., Cell 85: 683–693, 1996). The human $\alpha_v\beta_3$ integrin was diluted into coating buffer (CB) containing 150 mM NaCl, 1 mM CaCl$_2$, 1 mM MgCl$_2$, 1 mM MnCl$_2$, 20 mM TRIS, pH 7.4 at a concentration of 1.5 μg/ml. Into 96-well plates, 50 μl of the diluted integrin were added and allowed to bind to the plate walls overnight at 4° C. Next day, the assay plates were emptied and 100 μl of blocking buffer (CB buffer with 3% BSA) were added to each well for 45 min at 37° C. After the incubation, the plates were washed three times with 100 μl assay buffer (AB, CB buffer with 0.1% BSA). Serial 1:1 dilution (25 μl/well) of the test compounds were added to the plates, starting from 10 mM solutions in 100% DMSO diluted to 100 □M in AB. The binding reaction was started by addition (25 μl/well) of 10 nM biotinylated vitronectin (final concentration: 5 nM), and lasted 30 min at 37° C. The concentration range of the tested compounds spanned from 50 to 0.0005 μM. At the end of the co-incubation, the assay plates were washed as before and 70 μl of a 1:1000 AB dilution of peroxydase-conjugated streptavidin were added per well and were allowed to react for 45 min at 37° C. Then, the plates were washed as described and 50 μl of ready to use Turbo-TMB substrate for peroxydase were added to each well. After 30 minutes incubation at room temperature, the colour development was stopped with 50 μl sulphuric acid 0.38 M and the plates were read at a wavelength of 450 nm with a Packard plate reader. The values obtained were analyzed by four parameters curve fit in the computer program GraphPad Prism, after normalization by a maximum binding control (Bmax) detected in wells where no competitor was added, and a minimum binding control (NSB) detected in wells where no integrin was coated. Under standard assay conditions, A$_{450}$ was never under 1.0 for Bmax, and around 0.15 for NSB. The computerized algorithm gave the concentration of compound needed to inhibit the maximum binding by 50% (IC$_{50}$ value): for those compounds that did not inhibit this binding by 50% at the highest concentration tested, IC$_{50}$ value was reported as being greater then the highest concentration tested. As a positive control, increasing doses of a peptide containing the RGD sequence was added to each plate: IC$_{50}$ value of this molecule was 120 nM.

Materials

Human vitronectin receptor (□$_v$,□$_3$) was purified from human placenta (Pytela et al., Methods in Enzymology, 144: 475–489, 1987). Turbo-TMB was from PIERCE (34022). BSA (A4503), Vitronectin (V8379), RGD peptide (G4144) and all generic reagents were from SIGMA. Vitronectin was biotinylated according to the procedure indicated in the NHS biotinylation kit from PIERCE (21420). Horseradish peroxydase-streptavidin was from Amersham (RPN1231). 96-well plates were from Costar (#3690, EIA/RIA plate, ½ area flat bottom, high binding).

α$_{IIb}$β$_3$-fibrinogen Binding Assay

A solid phase assay for the study of α$_{IIb}$β$_3$-fibrinogen binding was set up on according to the method described for α$_v$β$_3$. α$_{IIb}$β$_3$ integrin was diluted into coating buffer (CB) containing 150 mM NaCl, 1 mM CaCl$_2$, 1 mM MgCl$_2$, 1 mM MnCl$_2$, 20 mM TRIS, pH 7.4 at a concentration of 3 μg/ml. Into 96-well plates, 50 μl of the diluted integrin were added and allowed to bind to the plate walls overnight at 4° C. Next day, the assay plates were emptied and 100 μl of blocking buffer (CB buffer with 3% BSA) were added to each well for 45 min at 37° C. After the incubation, the plates were washed three times with 100 μl assay buffer (AB, CB buffer with 0.1% BSA); serial 1:1 dilution (25 μl/well) of the test compounds were added to the plates, starting from 10 mM solutions in 100% DMSO diluted to 100 μM in AB. The binding reaction was started by addition (25 μl/well) of 20 nM biotinylated fibrinogen (final concentration: 10 nM), and lasted 30 min at 37° C. The concentration range of the tested compounds spanned from 50 to 0.0005 μM. At the end of the co-incubation, the assay plates were washed as before and 70 μl of a 1:1000 AB dilution of peroxydase-conjugated streptavidin were added per well and were allowed to react for 45 min at 37° C. Then, the plates were washed as described and 50 μl of ready to use Turbo-TMB substrate for peroxydase were added to each well. After 30 minutes incubation at room temperature, the colour development was stopped with 50 μl sulphuric acid 0.38 M and the plates were read at a wavelength of 450 nm with a Packard plate reader. The values obtained were analysed by four parameters curve fit with the computer program Graph-Pad Prism, after normalization by a maximum binding control (Bmax) detected in wells where no competitor was added, and a minimum binding control (NSB) detected in wells where no integrin was coated. Under standard assay conditions, A$_{450}$ was never under 0.8 for Bmax, and around 0.15 for NSB. The computerized algorithm gave the concentration of compound needed to inhibit the maximum binding by 50% (IC$_{50}$ value): for those compounds that did not inhibit this binding by 50% at the highest concentration tested, IC$_{50}$ value was reported as being greater then the highest concentration tested. As a positive control, increasing doses of a peptide containing the RGD sequence was added to each plate: IC$_{50}$ value of this molecule was 2.3 μM for α$_{IIb}$β$_3$-fibrinogen binding.

Materials

Human fibrinogen receptor (α$_{IIb}$β$_3$) was purified from human platelets ((Pytela et al., Methods in Enzymology, 144: 475–489, 1987). Turbo-TMB was from PIERCE (34022). BSA (A4503), fibrinogen (F4883), RGD peptide (G4144) and all generic reagents were from SIGMA. Fibrinogen was biotinylated according to the procedure indicated in the NHS biotinylation kit from PIERCE (21420). Horseradish peroxydase-streptavidin was from Amersham (RPN1231). 96-well plates were from Costar (#3690, EIA/RIA plate, ½ area flat bottom, high binding).

For example, compound (4-phenyl-6-{[3-(2-pyridinylamino)propanoyl]-amino}-3,4-dihydro-2H-1,4-benzoxazin-2-yl)acetic acid, 1a, and compound (4-phenyl-6-{[4-(2-pyridinylamino)butanoyl]amino}-3,4-dihydro-2H-1,4-benzoxazin-2-yl)acetic acid, 1b, when tested in α$_v$β$_3$-vitronectin and α$_{IIb}$β$_3$-fibrinogen binding assays, gave the following activity data:

Compound 1a:
α$_v$β$_3$ (IC$_{50}$ μmol)=0.044±0.025
α$_{IIb}$β$_3$ (IC$_{50}$ μmol)=30

Compound 1b:
α$_v$β$_3$ (IC$_{50}$ μmol)=0.024±0.009
α$_{IIb}$β$_3$ (IC$_{50}$ μmol)=27

These test data show that compounds 1a and 1b are endowed with high and selective α$_v$β$_3$ inhibiting activity. In fact, the ratio between α$_{IIb}$β$_3$ and α$_v$β$_3$ inhibiting activity is about 1,000.

In view of their highly selective α$_v$β$_3$ inhibiting or antagonizing activity, the compounds of the invention can be used in medicine for treating conditions mediated by the α$_v$β$_3$ integrin. Accordingly, the compounds of the invention are useful for instance for treating various conditions or disease states including osteoporosis, humoral hypercalcemia of malignancy, Paget's disease, tumor metastasis, solid tumor growth (neoplasia), angiogenesis including tumor angiogenesis, retinopathy including diabetic retinopathy, arthritis including rheumatoid arthritis, psoriasis, periodontal disease, smooth muscle cell migration and restenosis in a mammal in need of such treatment. Additionally, such pharmaceutical agents are useful as antiviral agents, and antimicrobials.

According to a preferred object of the invention the $\square_v,\square_3$ inhibiting activity results in an anticancer therapy having increased effectiveness in controlling, i.e., slowing, interrupting, arresting, stopping or reversing, the neoplasm formation.

The compounds of the invention can be administered in a variety of dosage forms, e.g. orally, in the form of tablets, capsules, sugar- or film-coated tablets, liquid solutions or suspensions; rectally, in the form of suppositories; parenterally, e.g. intramuscularly, or by intravenous injection of infusion; or topically.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regime may vary widely. Dosage levels of the order from about 0.01 mg to about 1000 mg per kilogram of body weight per day are useful in the treatment of the above-indicated conditions and more preferably of the order from about 0.01 mg to about 100 mg/kg of body weight. For instance, the dosage adopted for oral administration to adult humans for compound 1b may range from about 0.01 mg to about 800 mg/kg of body weight per day and more preferably of the order from about 0.01 mg to about 750 mg/kg body weight.

When given parenterally a suitable daily dose for instance for compound 1b would typically be about 0.01 to 100 mg/kg body weight injected per day in multiple doses depending on the factors listed above and more preferably from about 0.01 mg to about 10 mg/kg body weight.

The invention includes pharmaceutical compositions comprising a compound of formula (I) or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example by means of mixing, granulating, tabletting, sugar-coating or film-coating processes.

The liquid dispersion for oral administration may be, for instance syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethyl-cellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusion may contain as carrier, for example, sterile water or, preferably, they may be in the form of sterile aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

Compositions for topical application, e.g. creams, lotions or pastes, can be prepared by admixing the active ingredient with a conventional oleaginous or emulsifying excipient.

The following examples describe the invention without limiting it.

EXAMPLE 1

The preparations of (4-phenyl-6-{[3-(2-pyridinylamino)propanoyl]amino}-3,4-dihydro-2H-1,4-benzoxazin-2-yl)acetic acid, (4-phenyl-6-{[4-(2-pyridinyl-amino)butanoyl]3,4-amino}-dihydro-2H-1,4-benzoxazin-2-yl)acetic acid, and of (4-phenyl-6-{[5-(2-pyridinylamino)pentanoyl]amino}-3,4-dihydro-2H-1,4-benzoxazin-2-yl)acetic acid are provided. The synthetic procedures are described in Scheme 1 and Scheme 2.

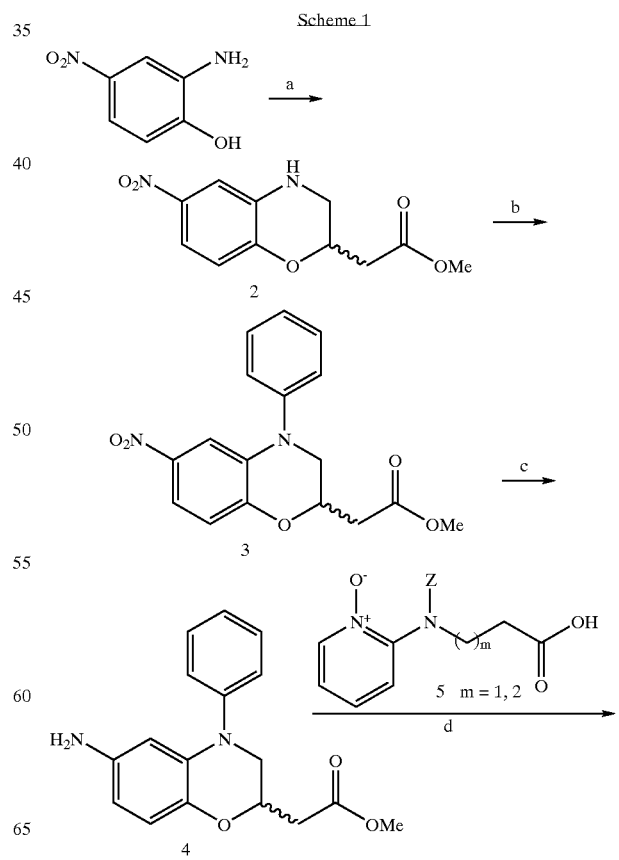

Scheme 1

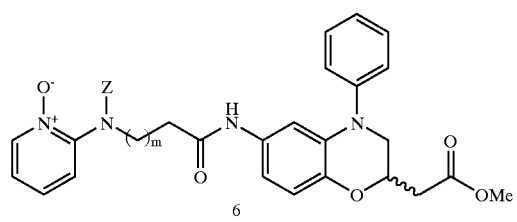

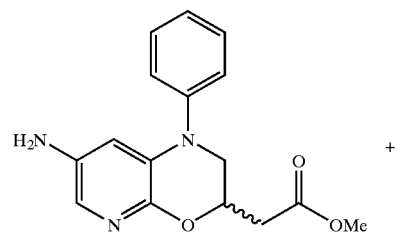

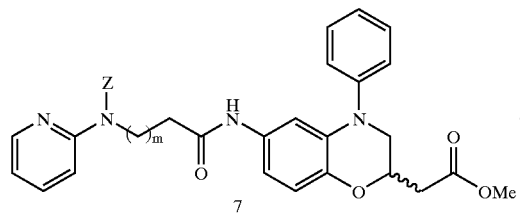

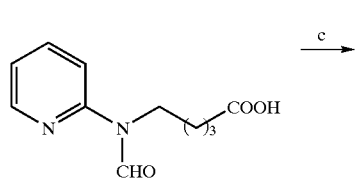

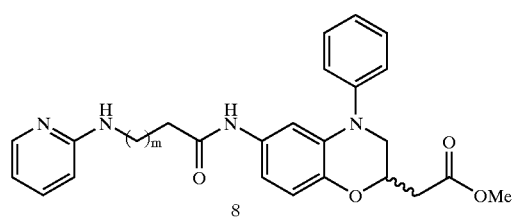

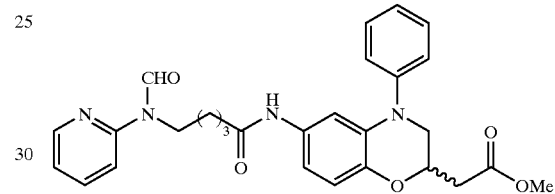

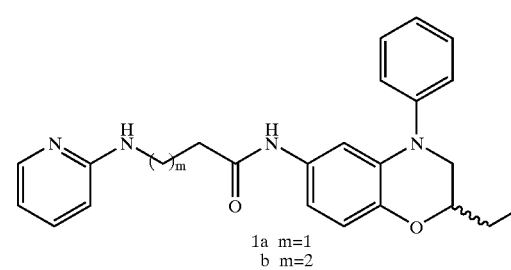

1a m=1
b m=2 a) methyl 4-bromo-2-butenoate, NaHCO$_3$, r.t. (91%);
b) 1,4-cyclohexandione, PTSA, toluene, reflux (25%);
c) 10% Pd/C, MeOH (56%);
d) EDCl, DMF, r.t. (76%);
e) TiCl$_4$/SnCl$_2$, THF (99%);
f) HCO$_2$NH$_4$, 10% Pd/C, THF/H$_2$O, r.t. (79%);
g) 1N NaOH, EtOH, r.t. (35%).

a) NaH, Br(CH$_2$)$_4$COOEt, DMF, 75° C. (30%); b) 1N NaOH (44%);
c) EDCl, DMF, r.t. (62%);d) 1N HCl, reflux (68%).

The synthesis of the ω-[N-carbobenzyloxy-N-(1-oxido-2-pyridinyl)]amino-acids 5 has been carried out as described in Scheme 3.

Scheme 2

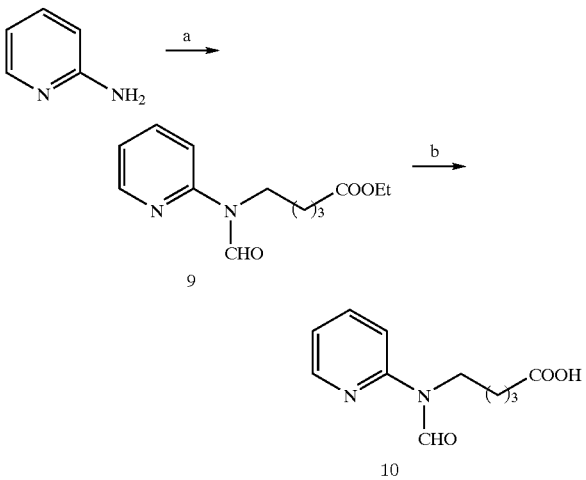

Scheme 3

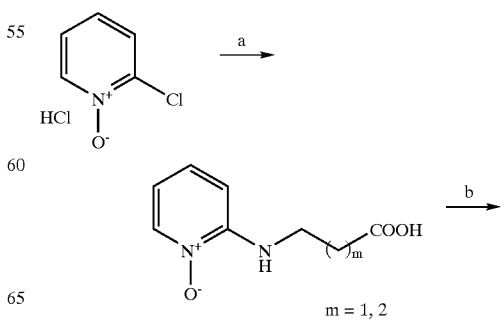

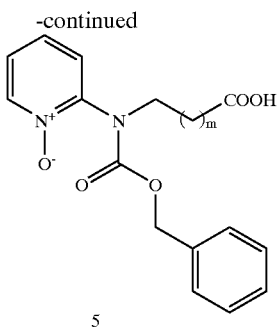

5 a) H$_2$N(CH$_2$)$_m$COOH, t-amyl- or isoamyl alcohol, reflux;
b) PhCH$_2$OCOCl, 2N NaOH (33–57%, overall);

(4-phenyl-6-{[3-(2-pyridinylamino)propanoyl]amino}-3,4-dihydro-2H-1,4-benzoxazin-2-yl)acetic acid, 1a

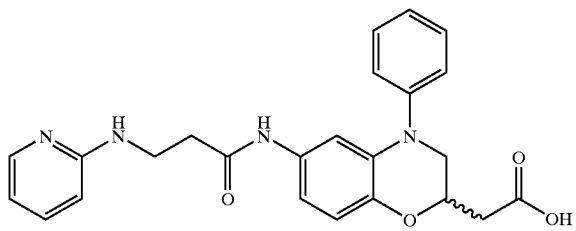

Methyl (6-nitro-3,4-dihydro-2H-1,4-benzoxazin-2-yl) acetate, 2

To a stirred suspension of 4-nitro-2-aminophenol (15.5 g, 100 mmol) and sodium hydrogen carbonate (10 g, 119 mmol) in methanol (100 mL), a solution of methyl-4-bromocrotonate (14 mL, 100 mmol) in methanol (50 mL) was added dropwise during 30 min, then stirring was continued for 4 h at room temperature. The reaction mixture was then concentrated in vacuo and partitioned between ethyl acetate (250 mL) and water (300 mL). After separation, the aqueous phase was newly extracted with ethyl acetate (2×250 mL). The combined extracts were dried (Na$_2$SO$_4$) and evaporated. The resulting oil was dissolved in ethanol (250 mL), potassium carbonate (5 g, 36 mmol) was added and the mixture was stirred for 4 h at room temperature. After evaporation, the resulting oil was diluted with dichloromethane (250 mL), washed with water (200 mL), then extracted whit 1N hydrochloric acid (150 mL). The aqueous solution was neutralised with 1N sodium hydroxide and extracted with ethyl acetate (3×250 mL). Finally, the combined extracts were dried (Na$_2$SO$_4$) and evaporated to dryness in vacuo to afford the title compound (23 g, 91%) as a red oil.

MS: m/z 294 (M+CH$_3$CN+H$^+$), 253 (M+H$^+$).
$^1$H-NMR (300 MHz), δ(CDCl$_3$): 2.74 (m, 2H), 3.25 (m, 1H), 3.55 (m, 1H), 3.75 (s, 3H), 4.1 (broad signal, 1H), 4.67 (m, 1H), 6.81 (d, 1H), 7.5 (d, 1H), 7.57 (dd, 1H).

Methyl (6-nitro-4-phenyl-3,4-dihydro-2H-1,4-benzoxazin-2-yl)acetate, 3

To a stirred suspension of 2 (23 g, 91 mmol) in toluene (150 mL), 1,4-cyclohexandione (11 g, 98 mmol) and p-toluenesulfonic acid were added. The resulting solution was stirred and refluxed for 4 h, using a condenser equipped with a Dean-Stark apparatus. The reaction mixture was then evaporated. The remaining oil was purified by flash chromatography (n-hexane/ethyl acetate 2:1) to afford compound 3 (7.5 g, 25%) as a red-orange oil that solidified on standing.

MS: m/z 329 (M+H$^+$).
$^1$H-NMR (300 MHz), δ(CDCl$_3$): 2.63–2.89 (m, 2H), 3.55 (m, 1H), 3.71 (s, 3H) 3.82 (m, 1H), 4.78 (m, 1H), 6.9 (d, 1H), 7.22 (m, 3H), 7.43 (m, 2H), 7.63 (dd, 1H), 7.69 (d, 1H).

Methyl (6-amino-4-phenyl-3,4-dihydro-2H-1,4-benzoxazin-2yl)acetate hydrochloride, 4

Compound 3 (7.5 g, 22.9 mmol) was dissolved in methanol (100 mL). After addition of 10% Pd/C (200 mg) and 37% hydrochloric acid (3 mL), the suspension was shaken in a Parr apparatus under a hydrogen atmosphere (50 psi) for 4 h. The reaction mixture was then filtered over Celite, and evaporated to small volume. Upon addition of diethyl ether (150 mL), compound 4 (4.3 g, 56%) precipitated as a light brown solid.

MS: m/z 299 (M+H$^+$).
$^1$H-NMR (300 MHz), δ(DMSO-d$_6$): 2.63–2.86 (m, 2H), 3.5 (m, 1H), 3.61 (s, 3H), 3.78 (m, 1H), 4.57 (m, 1H), 6.6 (dd, 1H), 6.7 (d, 1H), 6.84 (d, 1H), 7.18 (m, 1H), 7.26 (m, 2H), 7.41 (m, 2H), 9.4–9.58 (broad signal, 3H).

N-benzyloxycarbonyl-N-(1-oxido-2-pyridinyl)-beta-alanine, 5 (m=1)

2-Chloropyridine N-oxide hydrochloride (5 g, 30.1 mmol), β-alanine (13.36 g, 150 mmol) and sodium hydrogen carbonate (6.15 g, 73 mmol) were suspended in a mixture of isoamyl alcohol (100 mL) and water (7 mL), and refluxed for 48 hours. The reaction mixture was then cooled to room temperature and the solid was filtered off. The solid was washed with methanol (40 mL) and the filtrate was evaporated in vacuo. The solid obtained was then shaken in ethanol (100 mL), the insoluble solid filtered off, and the ethanol solution was evaporated in vacuo. The solid obtained was suspended in diethyl ether (50 mL), filtered and dried to give the desired crude product, as an extremely hygroscopic material, containing approximately 25% (NMR) of unreacted β-alanine. The crude material, without any further purification, was dissolved in aqueous 2N NaOH (77.5 mL, 155 mmol). The solution was cooled to 0° C. then, under vigorous stirring, benzyl chloroformate (13 mL, 92 mmol) was added dropwise. After 4 hours at 0° C., the reaction mixture was allowed to warm to room temperature then stirred overnight. The reaction mixture was then washed with Ethyl acetate (2×30 mL), acidified to pH 2 and extracted with Ethyl acetate (5×50 mL). The organic phase was dried over sodium sulfate and evaporated in vacuo. The residue was purified by flash chromatography (CH$_2$Cl$_2$/MeOH/AcOH: 95/5/0.5) to give 5 (m=1), as a light yellow oil (5.4 g, 57% overall).

MS: m/z 317 (M+H$^+$).
$^1$H-NMR (300 MHz), δ(DMSO-d$_6$): 2.5 (t, 2H, partially overlapped with DMSO), 3.7–3.82 (broad signal, 2H), 5.05 (s, 2H), 7.1–7.4 (m, 7H), 7.5 (m, 1H), 8.34 (m, 1H).

Methyl [6-({3-[N-benzyloxycarbonyl-N-(1-oxido-2-pyridinyl)amino]-propanoyl}amino)-4-phenyl-3,4-dihydro-2H-1,4-benzoxazin-2-yl]acetate, 6 (m=1)

To a stirred solution of N-(benzyloxycarbonyl)-N-(1-oxido-2-pyridinyl)-beta-alanine 5 (0.79 g, 2.5 mmol) in anhydrous DMF (15 mL) cooled to 0° C., compound 4 (0.9 g, 2.7 mmol), 4-dimethylaminopyridine (0.4 g. 3.3 mmol) and 1-ethyl-3-(3-dimethylaminopropyl)carbodiimide hydrochloride (0.6 g, 3.13 mmol) were added. After stirring for 1 h at 0° C., the solution was allowed to stand overnight at room temperature. Water (100 mL) was then added and the suspension was extracted with ethyl acetate (3×100 mL). The combined extract were dried (Na$_2$SO$_4$), evaporated and the resulting crude was purified by flash chromatography (ethyl acetate/methanol 9:1) to afford 6 (1.13 g, 76%).

MS: m/z 597 (M+H$^+$).
$^1$H-NMR (300 MHz), δ(CDCl$_3$): 2.5 (t, 2H), 2.56–2.83 (m, 2H), 3.48 (m, 1H), 3.7 (s, 3H), 3.75 (m, 1H), 3.98 (broad signal, 2H), 4.61 (m, 1H), 5.02 (broad s, 2H), 6.8 (m, 2H), 7.03–7.4 (m, 13H), 8.01 (broad s, 1H), 8.13 (d, 1H), 9 (broad s, 1H).

Methyl [6-({3-[N-(benzyloxycarbonyl)-N-(2-pyridinyl)amino]propanoyl}amino)-4-phenyl-3,4-dihydro-2H-1,4-benzoxazin-2-yl]acetate, 7 (m=1)

To a stirred solution of stannous chloride (0.44 g, 2.3 mmol) in anhydrous THF, under argon, a 1M dichloromethane solution of titanium(IV) chloride (2.3 ml, 2.3 mmol) was added dropwise at room temperature. After addition was completed, the reaction mixture was stirred 1 h at room temperature. A dichloromethane solution (15 mL) of 6 (1.12 g, 1.88 mmol) was added dropwise and stirring continued for 2 h. The reaction mixture was quenched whit water (100 mL), neutralised with 2N sodium hydroxide and the resulting solution was extracted with ethyl acetate (3×100 mL). The combined extracts were dried ($Na_2SO_4$), evaporated to dryness and the resulting compound 7 (1 g, 99%) was then submitted to the next step without further purification.

MS: m/z 581 (M+H$^+$).

Methyl (4-phenyl-6-{[3-(2-pyridinylamino)propanoyl]amino}-3,4-dihydro-2H-1,4-benzoxazin-2-yl)acetate, 8 (m=1)

To a stirred solution of 7 (1 g, 1.72 mmol) in THF/water 5:1 (25 ml), 10% Pd/C (100 mg) and ammonium formate (1 g, 15.86 mmol) were added at room temperature. Stirring was continued for 2 h, then the solution was filtered over Celite, diluted with ethyl acetate (100 mL), washed with brine, dried ($Na_2SO_4$), and evaporated to dryness. The resulting product was purified by flash chromatography on silica gel (ethyl acetate/n-hexane 4:1) to give the title compound (610 mg, 79.5%).

MS: m/z 447 (M+H$^+$).

(4-phenyl-6-{[3-(2-pyridinylamino)propanoyl]amino}-3,4-dihydro-2H-1,4-benzoxazin-2-yl)acetic acid, 1a To an ethanol (10 mL) solution of 8 (0.61 g, 1.37 mmol) 1N NaOH (3 mL) was added and the resulting solution was stirred for 1 h at room temperature. After neutralization with 1N hydrochloric acid, the mixture was extracted with ethyl acetate (3×50 mL) and dried. Partial evaporation of the solvent afforded a white precipitate that was collected to give 1a (0.2 g, 35%).

$^1$H-NMR (400 MHz), δ(DMSO-d$_6$): 2.44 (t, 2H, J=7.4, C$\underline{H}_2$CONH), 2.60 (m, 2H, C$\underline{H}_2$COOH), 4.41 (m, 1H, OC$\underline{H}$), 6.41 (m, 3H, H3'+H5'+NH), 6.69 (d, 1H, J=8.6, H-8 benzoxazine), 6.97 (dd, 1H, J=8.6, 2.3, H-7 benzoxazine), 7.09 (m, 1H), 7.20 (d, 1H, J=2.3, H-5 benzoxazine), 7.20–7.40 (m, 5H, aromatic hydrogens), 7.91 (m, 1H, H-6 pyridine); 9.57 (s, 1H, NHCO).

(4-phenyl-6-{[4-(2-pyridinylamino)butanoyl]amino}-3,4-dihydro-2H-1,4-benzoxazin-2-yl)acetic acid, 1b

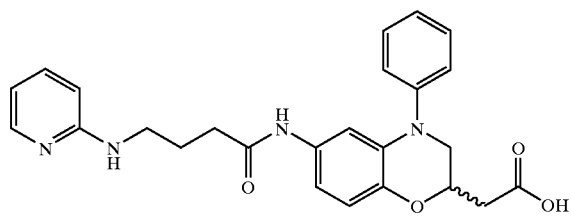

4-[N-(benzyloxycarbonyl)-N-(1-oxido-2-pyridinyl)amino]butanoic acid, 5 (m=2)

2-Chloropyridine N-oxide hydrochloride (15 g, 90.3 mmol), 4-amino-butanoic acid (46 g, 446 mmol) and sodium hydrogen carbonate (18.4 g, 219 mmol) were suspended in a mixture of tert-amyl alcohol (300 mL) and water (20 mL), and refluxed for 50 hours. The reaction mixture was then cooled at room temperature and the solid was filtered off. The solid was washed with methanol (70 mL) and the filtrate was evaporated in vacuo. The crude solid obtained was shaken in ethanol (300 mL), the insoluble solid was filtered off, and the ethanol solution was evaporated in vacuo. The solid obtained was suspended in diethyl ether (150 mL), filtered and dried to give N-(1-oxido-2-pyridinyl)amino]butanoic acid as a light yellow solid (15.7 g, 88.5%).

MS: m/z 197 (M+H$^+$).

$^1$H-NMR (300 MHz), δ(DMSO-d$_6$): 1.75 (m, 2H), 2.2 (t, 2H), 3.22 (q, 2H), 6.56 (dt, 1H), 6.8 (dd, 1H), 7.19 (m, 2H), 8.05 (dd, 1H).

4-[(1-oxido-2-pyridinyl)amino]butanoic acid (5 g, 25.5 mmol) was dissolved in aqueous 2N NaOH (100 mL, 200 mmol). The solution was cooled to 0° C. then, under vigorous stirring, benzyl chloroformate (17.6 mL, 124.8 mmol) was added dropwise. After 4 hours at 0° C., the reaction mixture was warmed at room temperature then stirred overnight. The reaction mixture was then washed with Ethyl acetate (2×50 mL), acidified until pH 2 and extracted with Ethyl acetate (5×50 mL). The organic phase was dried over sodium sulfate and evaporated in vacuo to give the crude product that was suspended in 30 mL of Ethyl acetate, filtered, washed with diethyl ether and dried to give the title compound (3.12 g, 37%).

MS: m/z 331 (M+H$^+$).

$^1$H-NMR (300 MHz), δ(DMSO-d$_6$): 1.62 (m, 2H), 2.25 (t, 2H), 3.5–3.67 (broad s, 2H), 5.05 (s, 2H), 7.2–7.4 (m, 7H), 7.56 (m, 1H), 8.3 (m, 1H).

Methyl [6-({4-[N-(benzyloxycarbonyl)-N-(1-oxido-2-pyridinyl)amino]butanoyl}amino)-4-phenyl-3,4-dihydro-2H-1,4-benzoxazin-2-yl]acetate, 6 (m=2)

To a stirred solution of 4-[N-(benzyloxycarbonyl)-N-(1-oxido-2-pyridinyl)amino]butanoic acid 5 (m=2, 0.6 g, 1.82 mmol) in anhydrous DMF (15 mL), cooled to 0° C., compound 4 (0.9 g, 2.7 mmol), 4-dimethylaminopyridine (0.4 g. 3.3 mmol) and 1-ethyl-3-(3-dimethylaminopropyl)carbodiimide hydrochloride (0.6 g, 3.13 mmol) were added. After stirring for 1 h at 0° C., the solution was allowed to stand overnight at room temperature. Water (100 mL) was then added and the suspension was extracted with ethyl acetate (3×100 mL). The combined extract were dried ($Na_2SO_4$), evaporated and the resulting crude product was purified by flash chromatography on silica gel (ethyl acetate/methanol 9:1) to afford 6 (m=2, 1.05 g, 94.5%).

MS: m/z 611 (M+H$^+$).

$^1$H-NMR (300 MHz), δ(CDCl$_3$): 1.61 (broad s, 2H), 2.42 (broad t, 2H), 2.55–2.85 (m, 2H), 3.46 (m, 1H), 3.7 (s, 3H), 3.75 (m, 3H), 4.62 (m, 1H), 5.1 (s, 2H), 6.78 (m, 1H), 7.01–7.41 (m, 14H), 8.01 (dd, 1H), 8.31 (broad s, 1H).

Methyl [6-({4-[N-(benzyloxycarbonyl)-N-(2-pyridinyl)amino]butanoyl}-amino)4-phenyl-3,4-dihydro-2H-1,4-benzoxazin-2-yl]acetate, 7 (m=2)

To a stirred solution of stannous chloride (0.38 g, 2 mmol) in anhydrous THF, under argon, a 1M dichloromethane solution of titanium(IV) chloride (2 mL) was added dropwise at room temperature. Once the addition was completed, the reaction mixture was stirred for 1 h at room temperature then a dichloromethane solution (15 mL) of 6 (m=2, 1 g, 1.64 mmol) was added dropwise and stirring continued for 2 additional hours. The reaction mixture was then quenched whit water (100 mL), neutralised with 2N NaOH and extracted with ethyl acetate (3×100 mL). The combined extracts were dried ($Na_2SO_4$), evaporated and the crude product (0.97 g, quantitative yield) was then submitted to the next step without further purification.

MS: m/z 595 (M+H$^+$).

Methyl (4-phenyl-6-{[4-(2-pyridinylamino)butanoyl]amino}-3,4-dihydro-2H-1,4-benzoxazin-2-yl)acetate, 8 (m=2)

To a stirred solution of 7 (m=2, 0.95 g, 1.6 mmol) in THF/water 5:1 (25 mL), 10% Pd/C (0.1 g) and ammonium formate (1 g) were added. Stirring was continued for 2 h, then the solution was filtered over Celite and diluted with ethyl acetate (100 mL), washed with brine, dried (Na$_2$SO$_4$), evaporated and the resulting product was purified by flash chromatography (ethyl acetate/n-hexane 4:1) to give 8 (m=2, 0.54 g, 73%).

MS: m/z 461 (M+H$^+$).

(4-phenyl-6-{[4-(2-pyridinylamino)butanoyl]amino}-3,4-dihydro-2H-1,4-benzoxazin-2-yl)acetic acid, 1b To an ethanol (10 mL) solution of 8 (m=2, 0.54 g, 1.17 mmol), 1N NaOH (3 mL) was added and the resulting solution was stirred for 1 h at room temperature. After neutralization with 1N HCl, the mixture was extracted with ethyl acetate (3×50 mL) and dried. The solution was partially evaporated. Collection of the precipitate afforded the title compound (0.185 g, 37%).

$^1$H-NMR (400 MHz), δ(DMSO-d$_6$): 1.75 (m, 2H, CH$_2$CH$_2$CH$_2$), 2.21 (t, 2H, J=7.4, CH$_2$CH$_2$CH$_2$CO), 2.60 (m, 2H, CH$_2$COOH), 4.42 (m, 1H, OCH), 6.40 (m, 3H, NH+H-3 and H-5 pyridine), 6.69 (d, 1H, J=8.6, H-8 benzoxazine), 6.97 (dd, 1H, J=8.6, 2.3, H-7 benzoxazine), 7.08 (m, 1H), 7.14 (d, 1H, J=2.3, H-5 benzoxazine), 7.20–7.40 (m, 5H, aromatic hydrogens), 7.89 (m, 1H, H-6 pyridine), 9.55 (s, 1H, NHCO).

4-phenyl-6-{[5-(2-pyridinylamino)pentanoyl]amino}-3,4-dihydro-2H-1,4-benzoxazin-2-yl)acetic acid, 1c

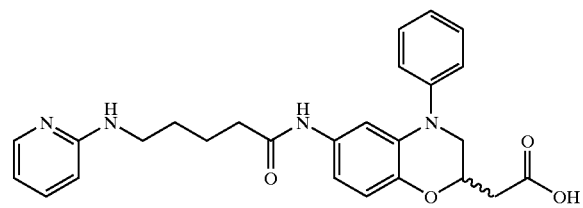

The compound has been synthesized as reported in Scheme 2.

Ethyl 5-[N-formyl-N-(2-pyridinyl)amino]pentanoate, 9

To a stirred suspension of 60% sodium hydride in mineral oil (2 g, 50 mmol) in DMF (160 mL), cooled to 0° C., 2-aminopyridine (3.94 g, 41.9 mmol), previously dissolved in DMF (20 mL), was added. After 15 minutes at 0° C., the suspension was warmed to room temperature, stirred for an additional hour, then ethyl 5-bromovalerate (8.4 mL, 209 mmol) was added. The reaction mixture was then heated at 75° C. overnight, cooled, concentrated in vacuo and poured into Ethyl acetate (100 mL). The organic phase was washed with water (50 mL), NaHCO$_3$ aqueous saturated solution (50 mL) and brine (50 mL), dried and concentrated to afford a deep brown oil (6 g) that was purified by flash chromatography (ethyl acetate/n-hexane: 1:1 then 7:3) to give 9 as a yellow oil (3.1 g, 30%).

MS: m/z 251 (M+H$^+$).

$^1$H-NMR (300 MHz), δ(CDCl$_3$): 1.21 (t, 3H), 1.65 (m, 4H), 2.3 (m, 2H), 3.93 (m, 2H), 4.07 (q, 2H), 7.02 (d, 1H), 7.1 (m, 1H), 7.7 (dt, 1H), 8.4 (dd, 1H), 9.18 (s, 1H).

5-[N-formyl-N-(2-pyridinyl)amino]pentanoic acid, 10

To a stirred solution of 9 (3.1 g, 12.4 mmol) in ethanol (120 mL), 1N NaOH (31 mL, 31 mmol) was added. After 3 hours at room temperature, the reaction mixture was quenched with 1N HCl until pH 7, then concentrated in vacuo. The residue was suspended in dichloromethane, filtered and the filtrate was newly evaporated. The crude product was purified by flash chromatography (ethyl acetate/n-hexane: 9/1) to afford the desired product 10 as a light yellow oil (1.2 g, 44%).

MS: m/z 223 (M+H$^+$).

$^1$H-NMR (300 MHz), δ(CDCl$_3$): 1.67 (m, 4H), 2.37 (m, 2H), 3.98 (m, 2H), 7.03 (d, 1H), 7.11 (m, 1H), 7.7 (dt, 1H), 8.4 (dd, 1H), 9.18 (s, 1H).

Methyl [6-({5-[N-formyl-N-(2-pyridinyl)amino]pentanoyl}amino)-4-phenyl-3,4-dihydro-2H-1,4-benzoxazin-2-yl]acetate, 11

To a stirred solution of 10 (0.6 g, 2.7 mmol) in anhydrous DMF (15 mL), cooled at 0° C., compound 4 (0.9 g, 2.7 mmol), 4-dimethylaminopyridine (0.4 g, 3.3 mmol) and 1-ethyl-3-(3-dimethylaminopropyl)carbodiimide hydrochloride (0.6 g, 3.13 mmol) were added. After stirring for 1 h at 0° C., the solution was allowed to stand overnight at room temperature. Water (100 mL) was then added and the suspension obtained was extracted with ethyl acetate (3×100 mL). The combined extract were dried (Na$_2$SO$_4$), evaporated and the resulting crude product was purified by flash chromatography on silica gel (ethyl acetate/n-exane 2:1) to afford compound 11 (0.835 g, 62%).

MS: m/z 503 (M+H$^+$).

$^1$H-NMR (300 MHz), δ(CDCl$_3$): 1.67 (m, 4H), 2.31 (broad t, 2H), 2.56–2.85 (m, 2H), 3.48 (m, 1H), 3.7 (s, 3H), 3.76 (m, 1H), 3.98 (broad t, 2H), 4.63 (m, 1H), 6.8 (d, 1H), 6.92 (dd, 1H), 7–7.4 (m, 8H), 7.7 (broad t, 1H), 8.37 (dd, 1H), 9.13 (broad s, 1H).

4-phenyl-6-{[5-(2-pyridinylamino)pentanoyl]amino}-3,4-dihydro-2H-1,4-benzoxazin-2-yl)acetic acid, 1c A suspension of 11 (0.83 g, 1.65 mmol) in 1N hydrochloric acid (5 mL), was heated at reflux for 1 h. The reaction mixture was then neutralised with 1N NaOH, extracted with ethyl acetate (3×50 mL) and dried. The solution was partially evaporated. Filtration of the precipitate formed afforded compound 1c (0.5 g, 68%).

$^1$H-NMR (400 MHz), δ(DMSO-d$_6$): 1.54 (m, 4H, CH$_2$CH$_2$CH$_2$), 2.18 (t, 2H, J=7.1, CH$_2$CH$_2$CH$_2$CH$_2$CO), 2.57 (m, 2H, CH$_2$COOH), 3.40 (m, 4H), 3.76 (m, 1H, PhNCH$_2$), 4.42 (m, 1H, OCH$_2$), 6.69 (d, 1H, J=8.7, H-8 benzoxazine), 6.97 (dd, 1H, J=2.3, 8.8, H-7 benzoxazine), 7.07 (m, 1H), 7.14 (d, 1H, J=2.3, H-5 benzoxazine), 7.20 (m, 2H), 7.34 (m, 1H, H-4 pyridine), 7.37 (m, 2H), 7.90 (m, 1H, H-6 pyridine), 9.51 (s, 1H, NHCO).

By analogous procedures the following compounds can be obtained:

(4-phenyl-6-{[3-(1H-imidazol-2-ylamino)propanoyl]amino}-3,4-dihydro-2H-1,4-benzoxazin-2-yl)acetic acid;
(4-phenyl-6-{[4-(1H-imidazol-2-ylamino)butanoyl]amino}-3,4-dihydro-2H-1,4-benzoxazin-2-yl)acetic acid;
(4-phenyl-6-{[5-(1H-imidazol-2-ylamino)pentanoyl]amino}-3,4-dihydro-2H-1,4-benzoxazin-2-yl)acetic acid.

EXAMPLE 2

The preparation of (4-benzyl-6-{[4-(2-pyridinylamino)butanoyl]amino}-3,4-dihydro-2H-1,4-benzoxazin-2-yl)acetic acid is described. The synthesis has been performed as described in Scheme 4.

Scheme 4

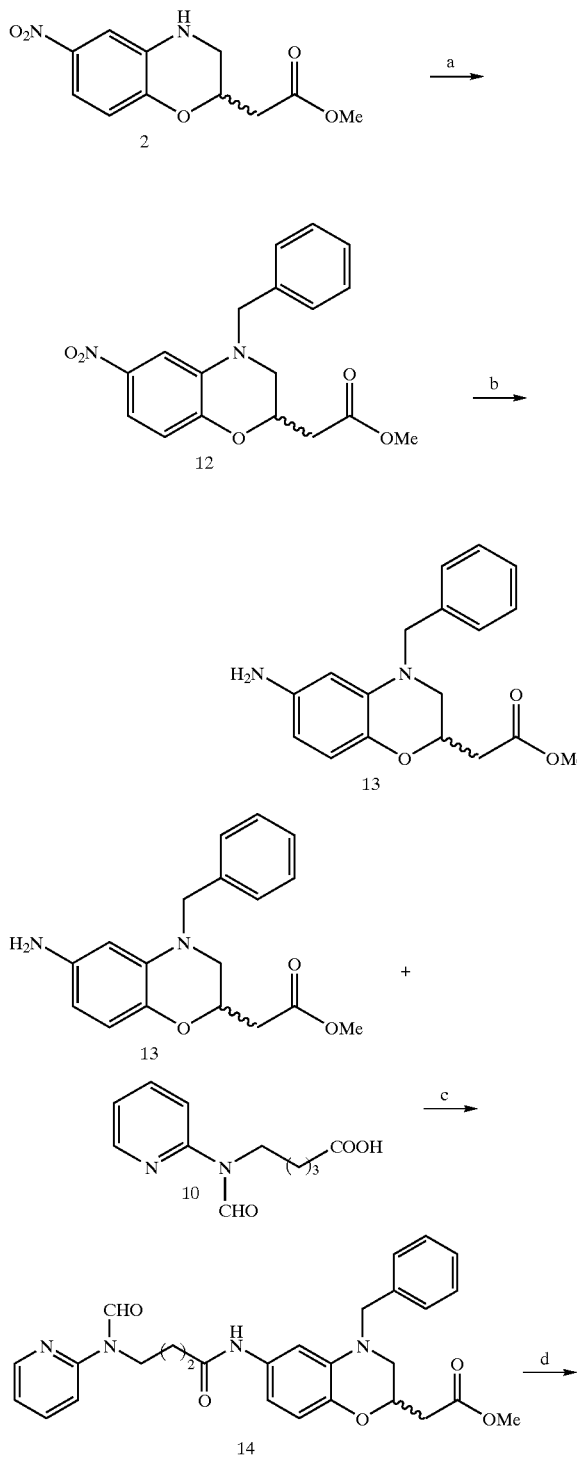

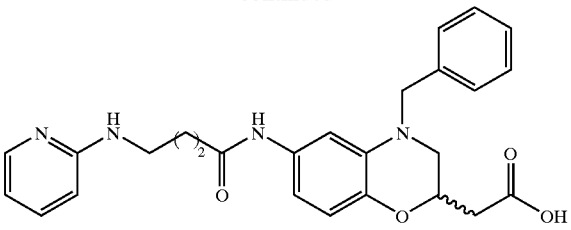

1d a) Na₂CO₃, BrCH₂Ph, DMF, 90° C. (66%);
b) Zn dust, AcOH/MeOH (90%);
c) EDCl, DMAP, DMF, r.t. (70%);
d) 1N HCl, reflux (60%).

(4-benzyl-6-{[4-(2-pyridinylamino)butanoyl]amino}-3,4-dihydro-2H-1,4-benzoxazin-2-yl)acetic acid, 1d

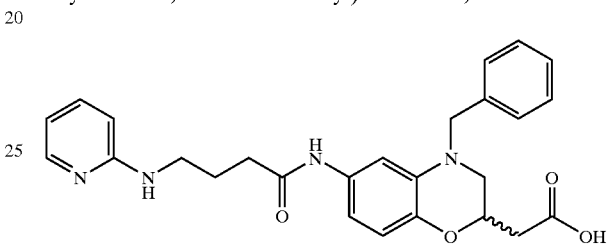

Methyl (4-benzyl-6-nitro-3,4-dihydro-2H-1,4-benzoxazin-2-yl)acetate, 12

To a stirred suspension of methyl (6-nitro-3,4-dihydro-2H-1,4-benzoxazin-2-yl)acetate 2 (2.52 g, 10 mmol) and anhydrous sodium carbonate (2 g.) in anhydrous DMF (15 mL), benzyl bromide (1.5 mL, 12.6 mmol) was added. The resulting suspension was stirred 2 hours at 90° C. The reaction mixture was then diluted with ethyl acetate (100 mL) and washed with water (3×100 mL). After separation, the organic phase was dried (Na₂SO₄) and evaporated to dryness in vacuo to afford the title compound (2.25 g, 66%) as a yellow-orange oil.

MS: m/z 343 (M+H)⁺, 685 (2M+H)⁺

¹H-NMR (300 MHz), δ(CDCl₃): 2.6–2.7 (m, 2H), 3.2 (m, 1H), 3.42 (m, 1H), 3.7 (s, 3H), 4.5 (m, 2H), 4.7 (m, 1H), 6.85 (d, 1H), 7.3 (m, 5H), 7.4 (m, 2H)

Methyl (6-amino-4-benzyl-3,4-dihydro-2H-1,4-benzoxazin-2-yl)acetate, 13

To a stirred solution of methyl (4-benzyl-6-nitro-3,4-dihydro-2H-1,4-benzoxazin-2-yl)acetate 12 (1.25 g, 3.7 mmol) in acetic acid (15 mL) and methanol (0.5 mL) at 0° C., zinc dust (1 g) was added. The suspension was stirred for 1 hour. After filtering under a pad of celite the solution was evaporated to dryness in vacuo. The residue was taken up with ethyl acetate (100 mL) and washed with saturated sodium hydrogen carbonate (100 mL), brine (2×100 mL) and then dried (Na₂SO₄) and evaporated to dryness in vacuo to afford the title compound (1 g, 90%) as a brown oil.

MS: m/z 313 (M+H)⁺

¹H-NMR (300 MHz), δ(CDCl₃): 2.6 (m, 2H), 3 (m, 1H), 3.2 (m, 1H), 3.7 (s, 3H), 4.25 (m, 2H), 4.5 (m, 1H), 6.4 (d, 1H), 6.6 (m, 5H), 6.7 (m, 2H)

Methyl [4-benzyl-6-({4-[N-formyl-N-(2-pyridinyl)amino]butanoyl}amino)-3,4-dihydro-2H-1,4-benzoxazin-2-yl]acetate, 14

To a stirred solution of 4-[formyl(2-pyridinyl)amino] butanoic acid 10 (265 mg, 1.27 mmol) in anhydrous DMF (15 mL) cooled at 0° C., methyl (6-amino-4-benzyl-3,4-dihydro-2H-1,4-benzoxazin-2-yl)acetate 13 (410 mg, 1.3 mmol), DMAP (250 mg.) and EDCl-HCl (300 mg, 1.6 mmol) were added. After stirring 1 hour at 0° C., the solution was allowed to stand overnight at room temperature. Water (100 mL) was then added and the suspension was extracted with ethyl acetate (3×100 mL). The combined extract were dried (Na$_2$SO$_4$), evaporated and the resulting crude was purified by flash chromatography on silica gel (ethyl acetate/n-hexane 4:1) to afford 14 (460 mg, 70%).

MS: m/z 503 (M+H)$^+$ $^1$H-NMR (300 MHz), δ(CDCl$_3$): 1.9 (broad triplet, 2H), 2.2 (broad triplet, 2H), 2.65–2.9 (m, 2H), 3.6 (s, 3H), 3.7 (m, 1H), 3.75 (m, 1H), 3.9 (broad triplet, 2H), 4.2 (m, 2H), 4.6 (m, 1H), 6.65 (dd, 1H), 6.85-7.7 (m, 10H), 8.3 (dd, 1H), 8.4 (broad singlet, 1H), 9.3 (broad singlet, 1H).

(4-benzyl-6-{[4-(2-pyridinylamino)butanoyl]amino}-3,4-dihydro-2H-1,4-benzoxazin-2-yl)acetic acid, 1d A solution of methyl [4-benzyl-6-({4-[formyl(2-pyridinyl)amino]butanoyl}amino)-3,4-dihydro-2H-1,4-benzoxazin-2-yl]acetate 14 (450 mg, 0.89 mmol) in 1N hydrochloric acid (5 mL) was refluxed for 1 hour. The resulting solution was cooled and after neutralization with 1N sodium hydroxide a white precipitate was obtained, which after washing and drying gave 1d (250 mg, 60%).

MS: m/z 461 (M+H)$^+$ $^1$H-NMR (300 MHz), δ(CDCl$_3$): 1.9 (broad triplet, 2H), 2.2 (broad triplet, 2H), 3.2 (m, 2H), 3.7 (m, 1H), 3.75 (m, 1H), 3.9 (broad triplet, 2H), 4.2 (m, 2H), 4.4 (m, 1H), 6.4 (m, 3H), 6.80 (d, 1H), 7.3 (m, 2H) 7.5 (m, 5H) 7.7 (broad singlet, 1H) 7.9 (m, 1H), 8.4 (broad singlet, 1H), 9.7 (broad singlet, 1H).

By analogous procedures, the following compounds can be obtained:

(4-benzyl-6-{[3-(2-pyridinylamino)propanoyl]amino}-3,4-dihydro-2H-1,4-benzoxazin-2-yl)acetic acid;
(4-benzyl-6-{[5-(2-pyridinylamino)pentanoyl]amino}-3,4-dihydro-2H-1,4-benzoxazin-2-yl)acetic acid;
(4-benzyl-6-{[3-(1H-imidazol-2-ylamino)propanoyl]amino}-3,4-dihydro-2H-1,4-benzoxazin-2-yl)acetic acid;
(4-benzyl-6-{[4-(1H-imidazol-2-ylamino)butanoyl]amino}-3,4-dihydro-2H-1,4-benzoxazin-2-yl)acetic acid;
(4-benzyl-6-{[5-(1H-imidazol-2-ylamino)pentanoyl]amino}-3,4-dihydro-2H-1,4-benzoxazin-2-yl)acetic acid;
(4-methyl-6-{[3-(2-pyridinylamino)propanoyl]amino}-3,4-dihydro-2H-1,4-benzoxazin-2-yl)acetic acid;
(4-methyl-6-{[4-(2-pyridinylamino)butanoyl]amino}-3,4-dihydro-2H-1,4-benzoxazin-2-yl)acetic acid;
(4-methyl-6-{[5-(2-pyridinylamino)pentanoyl]amino}-3,4-dihydro-2H-1,4-benzoxazin-2-yl)acetic acid;
(4-methyl-6-{[3-(1H-imidazol-2-ylamino)propanoyl]amino}-3,4-dihydro-2H-1,4-benzoxazin-2-yl)acetic acid;
(4-methyl-6-{[4-(1H-imidazol-2-ylamino)butanoyl]amino}-3,4-dihydro-2H-1,4-benzoxazin-2-yl)acetic acid;
(4-methyl-6-{[5-(1H-imidazol-2-ylamino)pentanoyl]amino}-3,4-dihydro-2H-1,4-benzoxazin-2-yl)acetic acid;
(4-cyclopropylmethyl-6-{[3-(2-pyridinylamino)propanoyl]amino}-3,4-dihydro-2H-1,4-benzoxazin-2-yl)acetic acid;
(4-cyclopropylmethyl-6-{[4-(2-pyridinylamino)butanoyl]amino}-3,4-dihydro-2H-1,4-benzoxazin-2-yl)acetic acid;
(4-cyclopropylmethyl-6-{[5-(2-pyridinylamino)pentanoyl]amino}-3,4-dihydro-2H-1,4-benzoxazin-2-yl)acetic acid;
(4-cyclopropylmethyl-6-{[3-(1H-imidazol-2-ylamino)propanoyl]amino}-3,4-dihydro-2H-1,4-benzoxazin-2-yl)acetic acid;
(4-cyclopropylmethyl-6-{[4-(1H-imidazol-2-ylamino)butanoyl]amino}-3,4-dihydro-2H-1,4-benzoxazin-2-yl)acetic acid;
(4-cyclopropylmethyl-6-{[5-(1H-imidazol-2-ylamino)pentanoyl]amino}-3,4-dihydro-2H-1,4-benzoxazin-2-yl)acetic acid;
(4-cyclohexylmethyl-6-{[3-(2-pyridinylamino)propanoyl]amino}-3,4-dihydro-2H-1,4-benzoxazin-2-yl)acetic acid;
(4-cyclohexylmethyl-6-{[4-(2-pyridinylamino)butanoyl]amino}-3,4-dihydro-2H-1,4-benzoxazin-2-yl)acetic acid;
(4-cyclohexylmethyl-6-{[5-(2-pyridinylamino)pentanoyl]amino}-3,4-dihydro-2H-1,4-benzoxazin-2-yl)acetic acid;
(4-cyclohexylmethyl-6-{[3-(1H-imidazol-2-ylamino)propanoyl]amino}-3,4-dihydro-2H-1,4-benzoxazin-2-yl)acetic acid;
(4-cyclohexylmethyl-6-{[4-(1H-imidazol-2-ylamino)butanoyl]amino}-3,4-dihydro-2H-1,4-benzoxazin-2-yl)acetic acid;
(4-cyclohexylmethyl-6-{[5-(1H-imidazol-2-ylamino)pentanoyl]amino}-3,4-dihydro-2H-1,4-benzoxazin-2-yl)acetic acid.

EXAMPLE 3

The preparation of (4-benzoyl-6-{[4-(2-pyridinylamino)butanoyl]amino}-3,4-dihydro-2H-1,4-benzoxazin-2-yl)acetic acid is described. The synthesis has been performed as described in Scheme 5.

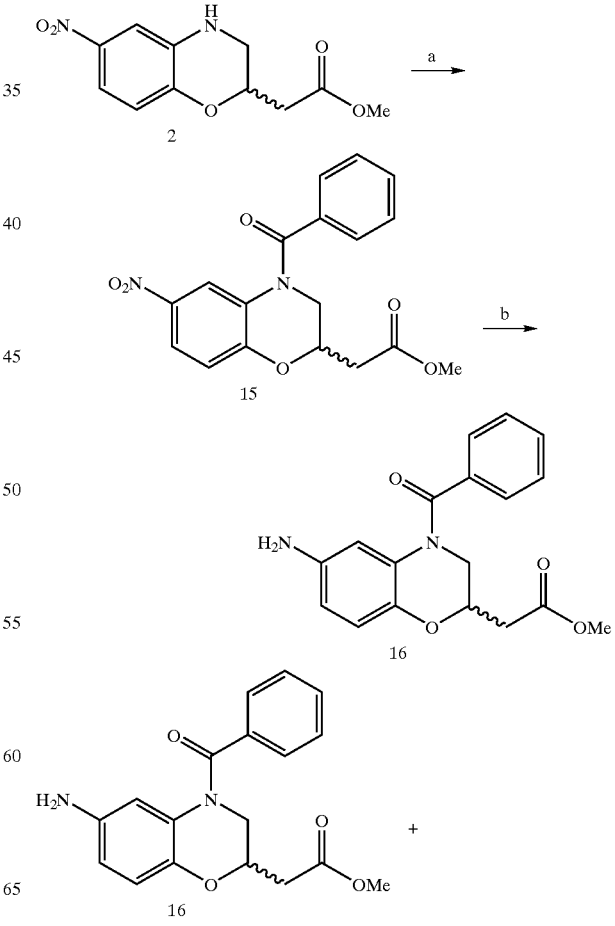

Scheme 5

-continued

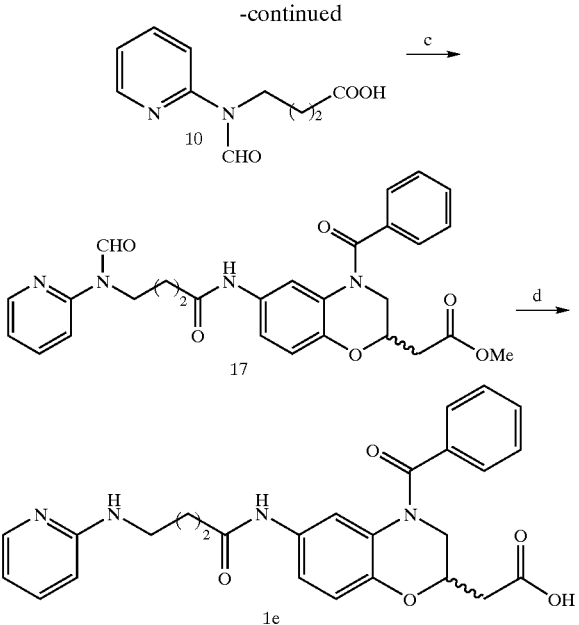

a) Na₂CO₃, PhCOCl, DMF, r.t. (93%);
b) Zn dust, AcOH/MeOH (90%);
c) EDCl, DMAP, DMF, r.t. (60%);
d) 1N HCl, reflux (20%).

(4-benzoyl-6-{[4-(2-pyridinylamino)butanoyl]amino}-3,4-dihydro-2H-1,4-benzoxazin-2-yl)acetic acid, 1e

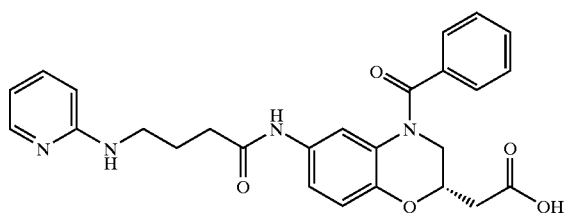

Methyl (4-benzoyl-6-nitro-3,4-dihydro-2H-1,4-benzoxazin-2-yl)acetate, 15

To a stirred suspension of methyl (6-nitro-3,4-dihydro-2H-1,4-benzoxazin-2-yl)acetate 2 (2.52 g, 10 mmol) and anhydrous sodium carbonate (2 g.) in anhydrous DMF (15 mL) and anhydrous pyridine (5 mL), benzoyl chloride (1.5 mL, 12.96 mmol) was added. The resulting suspension was stirred 8 hours at room temperature. The reaction mixture was then diluted with ethyl acetate (100 mL) and washed with water (3×100 mL). After separation the organic phase was dried (Na₂SO₄) and evaporated to dryness in vacuo to afford the title compound (3.3 g, 93%) as a yellow-orange oil.

MS: m/z 357 (M+H)⁺, 374 (M+NH₄)⁺

¹H-NMR (300 MHz), δ(CDCl₃): 2.58–2.64 (m, 2H), 3.30 (m, 1H), 3.64 (m, 1H), 3.7 (s, 3H), 5.10 (m, 1H), 6.88 (d, 1H), 7.3 (m, 5H), 7.7 (m, 2H)

Methyl (4-benzoyl-6-amino-3,4-dihydro-2H-1,4-benzoxazin-2-yl)acetate, 16

To a stirred solution of 15 (1.65 g, 4.6 mmol) in acetic acid (15 mL) and methanol (0.5 mL) at 0° C., zinc dust (2 g) was added. The suspension was stirred for 1 hour. After filtering under a pad of celite the solution was evaporated to dryness in vacuo. The residue was taken up with ethyl acetate (100 mL) and washed with saturated sodium hydrogen carbonate (100 mL), brine (2×100 mL) and then dried (Na₂SO₄) and evaporated to dryness in vacuo to afford the title compound (1.3 g, 90%) as a brown oil.

MS: m/z 327 (M+H)⁺, 653 (2M+H)⁺

¹H-NMR (300 MHz), δ(CDCl₃): 2.4–2.5 (m, 2H), 3-3.5 (m, 2H), 3.6 (s, 3H), 4.3 (m, 1H), 6.5 (m, 2H), 7.2–7.6 (m, 6H).

Methyl [4-benzoyl-6-({4-[N-formyl-N-(2-pyridinyl)amino]butanoyl}amino)-3,4-dihydro-2H-1,4-benzoxazin-2-yl]acetate, 17

To a stirred solution of 4-[formyl(2-pyridinyl)amino]butanoic acid 10 (265 mg, 1.27 mmol) in anhydrous DMF (15 mL) cooled at 0° C., methyl (6-amino-4-benzoyl-3,4-dihydro-2H-1,4-benzoxazin-2-yl)acetate 16 (430 mg, 1.3 mmol), DMAP (250 mg) and EDCl-HCl (300 mg, 1.6 mmol) were added. After stirring 1 hour at 0° C., the solution was allowed to stand overnight at room temperature. Water (100 mL) was then added and the suspension was extracted with ethyl acetate (3×100 mL). The combined extract were dried (Na₂SO₄), evaporated and the resulting crude was purified by flash chromatography on silica gel (ethyl acetate/n-hexane 5:1) to afford compound 17 (420 mg, 60%).

MS: m/z 517 (M+H)⁺

¹H-NMR (300 MHz), δ(CDCl₃): 1.95 (broad triplet, 2H), 2.3 (broad triplet, 2H), 2.58–2.85 (m, 2H), 3.6 (m, 1H), 3.7 (s, 3H), 3.75 (m, 1H), 3.98 (broad triplet, 2H), 4.75 (m, 1H), 6.85 (d, 1H), 7.15–7.75 (m, 10H), 8.4 (dd, 1H), 8.1 (broad singlet 1H), 9.15 (broad singlet, 1H).

(4-benzoyl-6-{[4-(2-pyridinylamino)butanoyl]amino}-3,4-dihydro-2H-1,4-benzoxazin-2-yl)acetic acid, 1e A solution of 17 (280 mg, 0.54 mmol) in 1N hydrochloric acid (5 mL) was refluxed for 1 hour. The resulting solution was cooled and after neutralization with 1N sodium hydroxide a white precipitate was obtained, which after washing and drying gave compound 1e (50 mg, 20%).

MS: m/z 475 (M+H)⁺

By analogous procedures the following compounds can be obtained:

(4-benzoyl-6-{[3-(2-pyridinylamino)propanoyl]amino}-3,4-dihydro-2H-1,4-benzoxazin-2-yl)acetic acid;
(4-benzoyl-6-{[5-(2-pyridinylamino)pentanoyl]amino}-3,4-dihydro-2H-1,4-benzoxazin-2-yl)acetic acid;
(4-benzoyl-6-{[3-(1H-imidazol-2-ylamino)propanoyl]amino}-3,4-dihydro-2H-1,4-benzoxazin-2-yl)acetic acid;
(4-benzoyl-6-{[4-(1H-imidazol-2-ylamino)butanoyl]amino}-3,4-dihydro-2H-1,4-benzoxazin-2-yl)acetic acid;
(4-benzoyl-6-{[5-(1H-imidazol-2-ylamino)pentanoyl]amino}-3,4-dihydro-2H-1,4-benzoxazin-2-yl)acetic acid;
(4-nicotinoyl-6-{[3-(2-pyridinylamino)propanoyl]amino}-3,4-dihydro-2H-1,4-benzoxazin-2-yl)acetic acid;
(4-nicotinoyl-6-{[4-(2-pyridinylamino)butanoyl]amino}-3,4-dihydro-2H-1,4-benzoxazin-2-yl)acetic acid;
(4-nicotinoyl-6-{[5-(2-pyridinylamino)pentanoyl]amino}-3,4-dihydro-2H-1,4-benzoxazin-2-yl)acetic acid;
(4-nicotinoyl-6-{[3-(1H-imidazol-2-ylamino)propanoyl]amino}-3,4-dihydro-2H-1,4-benzoxazin-2-yl)acetic acid;
(4-nicotinoyl-6-{[4-(1H-imidazol-2-ylamino)butanoyl]amino}-3,4-dihydro-2H-1,4-benzoxazin-2-yl)acetic acid;
(4-nicotinoyl-6-{[5-(1H-imidazol-2-ylamino)pentanoyl]amino}-3,4-dihydro-2H-1,4-benzoxazin-2-yl)acetic acid;

EXAMPLE 4

The preparation of (4-phenyl-6-{[3-(2-pyridinylamino)propylamino]carbonyl}-3,4-dihydro-2H-1,4-benzoxazin-2-yl)acetic acid is described. The synthesis has been performed as described in Scheme 6.

Scheme 6

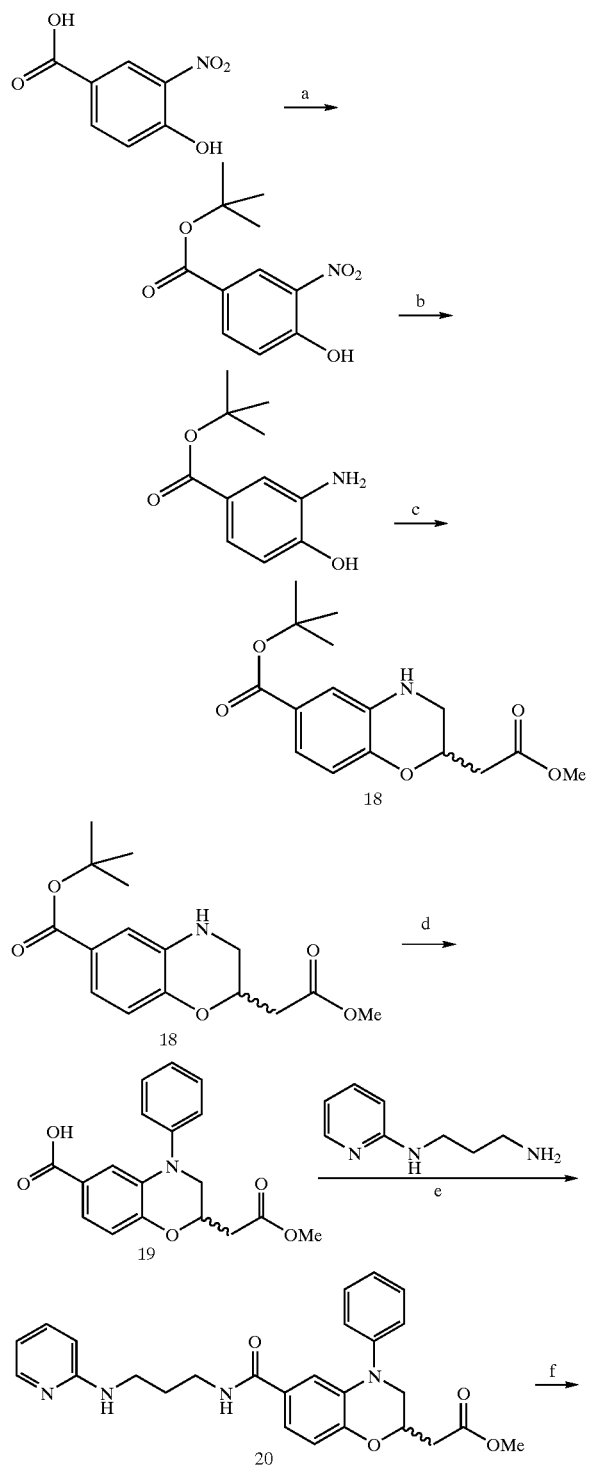

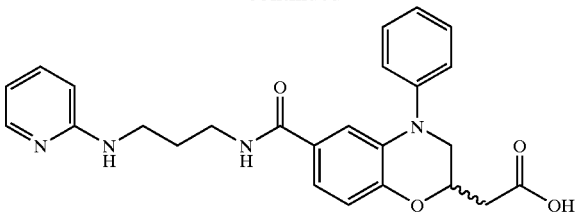

1f a) t-butanol, H₂SO₄, MgSO₄, r.t. (90%);
b) H₂, Pd/C, MeOH (95%);
c) methyl 4-bromo-2-butenoate, NaHCO3, r.t. (91%);
d) 1,4-cyclohexandione, PTSA, toluene, reflux (52%);
e) EDCl, DMF, r.t. (20%);
f) 1N NaOH, EtOH, r.t. (43%).

tert-butyl 4-hydroxy-3-nitrobenzoate

Magnesium sulfate anhydrous (9.62 g, 80 mmol) was suspended at room temperature in dichloromethane (50 mL) and 96% sulfuric acid (1.1 mL, 20 mmol) was added, the mixture was vigorously stirred for 15 min and then 4-hydroxy-3-nitrobenzoic acid (3.7 g, 20.22 mmol) and tert-butanol (9.6 mL, 100 mmol) were added. Stirring was continued for 48 hours. A saturated sodium hydrogen carbonate solution (150 mL) was slowly added and the mixture was diluted with dichloromethane (150 mL). The organic layer was separated and dried (Na₂SO₄), evaporated to afford tert-butyl 4-hydroxy-3-nitrobenzoate as a yellow solid (4.43 g, 90%).

MS: m/z 238 (M−H)⁻

$^1$H-NMR (300 MHz), δ(CDCl₃): 1.7 (s, 9H), 7.2 (d, 1H), 8.2 (d, 1H), 8.75 (s, 1H), 10.8 (broad singlet, 1H).

tert-butyl 4-hydroxy-3-aminobenzoate

To a solution of tert-butyl 4-hydroxy-3-nitrobenzoate (4.4 g, 18.4 mmol) in methanol (50 mL), 10% Pd/C (200 mg) was added and the resulting suspension was hydrogenated at 50 psi for 4 hours. After filtering under a pad of celite, methanol was removed in vacuo to obtain the title compound as a greenish powder (3.5 g, 95%).

MS: m/z 210 (M+H)⁺, 419 (2M+H)⁺, 208 (M−H)⁻

$^1$H-NMR (300 MHz), δ(CDCl₃): 1.7 (s, 9H), 4.2 (broad singlet, 2H) 6.75 (d, 1H), 7.6 (m, 2H).

Methyl (6-tert-butoxycarbonyl-3,4-dihydro-2H-1,4-benzoxazin-2-yl)acetate, 18

To a stirred solution of tert-butyl 4-hydroxy-3-aminobenzoate (3 g, 14.35 mmol) in methanol (20 mL) sodium hydrogen carbonate (1.5 g) was added and a solution of methyl-4-bromo crotonate (3 mL, 17 mmol) in methanol (5 mL) was added dropwise in 30 minutes and the resulting suspension was stirred 4 h at room temperature. The reaction mixture was concentrated in vacuo and taken up with ethyl acetate (250 mL) and water (300 mL). The organic phase was separated and the aqueous phase was extracted with more ethyl acetate (2×250 mL). The combined extracts were dried (Na₂SO₄) evaporated and the resulting oil dissolved in ethanol (25 mL), potassium carbonate (1 g) was added and the resulting suspension was stirred 4 h at room temperature. The reaction mixture was evaporated in vacuo and the resulting oil was diluted with dichloromethane (150 mL) and washed with water (3×100 mL), the organic solution was then extracted whit hydrochloric acid 1N (150 mL) and separated, the aqueous solution was neutralized with 1N sodium hydroxide and extracted with ethyl acetate (3×150 mL). The combined extract were dried (Na₂SO₄) evaporated to dryness in vacuo, the resulting crude was purified by flash chromatography on silica gel (n-hexane/ethyl acetate 3:1) to afford tert-butyl 2-(2-methoxy-2-oxoethyl)-3,4-dihydro-2H-1,4-benzoxazine-6-carboxylate (5.4 g) as a white solid.

MS: m/z 308 (M+H)+, 615 (2M+H)+, 306 (M−H)−, 366 (M+AcOH−H)−.

1H-NMR (300 MHz), δ(CDCl3): 1.55 (s, 9H), 2.6 (m, 1H), 2.8 (m, 1H), 3.2 (m, 1H), 3.45 (m, 1H), 3.75 (s, 3H), 4.65 (m, 1H), 6.8 (dd, 1H), 7.25 (dd, 1H), 7.35 (dd, 1H).

2-(2-methoxy-2-oxoethyl)-4-phenyl-3,4-dihydro-2H-1,4-benzoxazine-6-carboxylic acid, 19

To a stirred suspension of tert-butyl 2-(2-methoxy-2-oxoethyl)-3,4-dihydro-2H-1,4-benzoxazine-6-carboxylate (5.3 g, 17.3 mmol) in toluene (50 mL) 1,4-cyclohexandione (2.8 g, 25 mmol) and p-toluenesulfonic acid (1 g) were added. The resulting solution was stirred at reflux for 4 hours, using a condenser equipped with a Dean-Stark apparatus. The reaction mixture was concentrated in vacuo. The remaining oil was purified by flash chromatography on silica gel column eluting with ethyl acetate to give 2-(2-methoxy-2-oxoethyl)-4-phenyl-3,4-dihydro-2H-1,4-benzoxazine-6-carboxylic acid (2.9 g, 52%) as a white solid.

MS: m/z 328 (M+H)+, 655 (2M+H)+, 306 (M−H)−

1H-NMR (300 MHz), δ(CDCl3): 2.65 (m, 1H), 2.85 (m, 1H), 3.55 (m, 1H), 3.7 (s, 3H), 3.85 (m, 1H), 4.75 (m, 1H), 6.9 (d, 1H), 7.15–7.4 (m, 5H), 7.45 (dd, 1H), 7.6 (d, 1H).

N-(2-pyridinyl)-1,3-propanediamine

A mixture of 2-bromopyridine (12.3 mL, 126.7 mmol) and pyridine (13 mL, 161 mmol) in 1,3-diaminopropane (53.5 mL, 640 mmol) was refluxed under nitrogen for 18 hours. The reaction mixture was evaporated under reduced pressure and cooled, and the resulting residue was treated with THF (150 mL) to yield a white precipitate. The precipitate was filtered and washed with additional THF (100 mL). Evaporation of the filtrate afforded an orange oil, which was distilled in vacuo to give N-(2-pyridinyl)-1,3-propanediamine (9.6 g, 50%) as a colorless oil: bp 128–132° C. (2 mmHg).

MS: m/z 152 (M+H)+

1H-NMR (300 MHz), δ(CDCl3): 1.28 (broad singlet, 2H), 1.75 (m, 2H), 2.84 (t, 2H), 3.35 (m, 2H) 5.00 (broad singlet, 1H) 6.50 (m, 2H) 7.40 (dd, 1H), 8.07 (1H, Methyl [4-phenyl-6-{[3-(2-pyridinylamino)propylamino] carbonyl}-3,4-dihydro-2H-1,4-benzoxazin-2-yl]acetate, 20

To a stirred solution of 2-(2-methoxy-2-oxoethyl)-4-phenyl-3,4-dihydro-2H-1,4-benzoxazine-6-carboxylic acid (330 mg, 1 mmol) in anhydrous DMF (15 mL) cooled at 0° C., N-(2-pyridinyl)-1,3-propanediamine (200 mg, 1.3 mmol), DMAP (150 mg) and EDCl-HCl (300 mg, 1.6 mmol) were added. After stirring 1 hour at 0° C., the solution was allowed to stand overnight at room temperature. Water (100 mL) was then added and the suspension was extracted with ethyl acetate (3×100 mL). The combined extract were dried (Na2SO4), evaporated and the resulting crude was purified by flash chromatography on silica gel (ethyl acetate/n-hexane 4:1) to afford the title compound (100 mg, 20%) as a white solid.

MS: m/z 461 (M+H)+

[4-phenyl-6-{[3-(2-pyridinylamino)propylamino] carbonyl}-3,4-dihydro-2H-1,4-benzoxazin-2-yl]acetic acid, 1f To a stirred solution of compound 20 (80 mg, 0.17 mmol) in ethanol (10 mL) were added 0.18 mL of 1N NaOH solution. The reaction mixture is stirred at room temperature for 3 hours and left standing overnight. After neutralization with 2N HCl (0.08 mL), absolute ethanol is added (10 mL) is added, the solution is evaporated in vacuo and the residue is purified by filtration trough a small pad of silica gel, eluting with dichloromethane and methanol (8:2) to give 33 mg (43%) of the title compound.

MS:: m/z 447 (M+H)+

According to the same procedure, the following compounds can be prepared:

[4-phenyl-6-{[2(2-pyridinylamino)ethylamino]carbonyl}-3,4-dihydro-2H-1,4-benzoxazin-2-yl]acetic acid;
[4-phenyl-6-{[4-(2-pyridinylamino)butylamino]carbonyl}-3,4-dihydro-2H-1,4-benzoxazin-2-yl]acetic acid;
[4-phenyl-6-{[2(1H-imidazol-2-ylamino)ethylamino]carbonyl}-3,4-dihydro-2H-1,4-benzoxazin-2-yl]acetic acid;
[4-phenyl-6-{[3-(1H-imidazol-2-ylamino)propylamino]carbonyl}-3,4-dihydro-2H-1,4-benzoxazin-2-yl]acetic acid;
[4-phenyl-6-{[4-(1H-imidazol-2-ylamino)butylamino]carbonyl}-3,4-dihydro-2H-1,4-benzoxazin-2-yl]acetic acid.

EXAMPLE 5

Capsules, each dosed at 0.200 g and containing 20 mg of the active substance can be prepared.

| Composition for 500 capsules: | |
| --- | --- |
| (4-phenyl-6-{[4-(2-pyridinylamino) butanoyl]amino}-3,4-dihydro-2H-1,4-benzoxazin-2-yl)acetic acid | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

EXAMPLE 6

Tablets, each weighing 0.150 g and containing 25 mg of the active substance, can be manufactured as follows.

| Composition for 10,000 tablets: | |
| --- | --- |
| (4-phenyl-6-{[3-(2-pyridinylamino) butanoyl]amino}-3,4-dihydro-2H-1,4-benzoxazin-2-yl)acetic acid | 250 g |
| Lactose | 800 g |
| Corn starch | 415 g |
| Talc powder | 30 g |
| Magnesium stearate | 5 g |

The (4-phenyl-6-{[3-(2-pyridinylamino)butanoyl] amino}-3,4-dihydro-2H-1,4-benz-oxazin-2-yl)acetic acid, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 7

Intravenous infusion 1–10 mg/ml. An intravenous infusion pharmaceutical preparation can be manufactured by dissolving 50 mg of (4-phenyl-6-{[3-(2-pyridinylamino) butanoyl]amino}-3,4-dihydro-2H-1,4-benzoxazin-2-yl) acetic acid in water for injection (1000 ml) and sealing glass ampoules of 1–10 ml. Prior to infusion, the obtained solution can be diluted according to the common practice, and stored and/or delivered in glass, polypropylene, polyolefin or polyethylene-lined equipment.

What is claimed is:

1. A compound of formula (I):

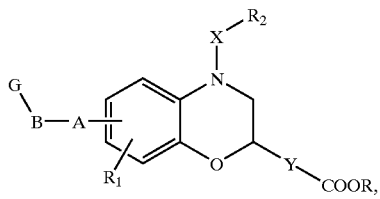

or a pharmaceutically acceptable salt or ester thereof, wherein:

G is selected from the group consisting of:

a) 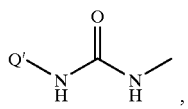

b) 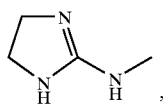

c) 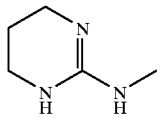

d) 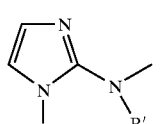

e) 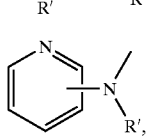

f) 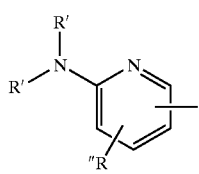

g) 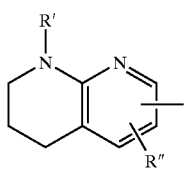

Q is NH or O;
Q' is selected from the group consisting of H, $C_1$–$C_6$ alkyl, phenyl, and phenyl-$C_1$–$C_4$-alkyl;
R' and R" are independently H or $C_1$–$C_4$-alkyl;
B is $C_1$–$C_4$ alkyl or $C_2$–$C_4$ alkenyl;
A is selected from the group consisting of $CH_2$, O, $S(O)_p$, NH, CON(R'''), and N(R''')CO;

p is zero, 1 or 2;
R''' is hydrogen or $CH_3$;
$R_1$ is selected from the group consisting of H, $C_1$–$C_4$ alkyl, $C_1$–$C_4$ alkoxy, OH, halogen, and $CF_3$;
X is C=O or a bond, except that X is C=O when G is:

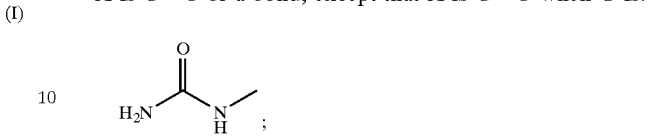

$R_2$ is selected from the group consisting of:
H;
$C_1$–$C_4$ alkyl;
$C_3$–$C_7$ cycloalkyl;
$C_1$–$C_4$-alkylcycloalkyl;
aryl optionally substituted by one to three substituents independently selected from the group consisting of halogen, $CF_3$, $C_1$–$C_4$ alkyl, hydroxy, and $C_1$–$C_4$ alkoxy;
aralkyl; and
a heteroaryl selected from the group consisting of pyridinyl, pyrazinyl, pyridazinyl, pyrimidinyl, thienyl, pyrrolyl, pyrazolyl, imidazolyl, oxazolyl, and isoxazolyl, wherein:
any such heteroaryl is optionally substituted by one to three substituents independently selected from the group consisting of halogen, $CF_3$, $C_1$–$C_4$ alkyl, hydroxy, and $C_1$–$C_4$ alkoxy;
Y is $(CH_2)_n$;
n is 1 or 2; and
R is selected from the group consisting of hydrogen, $C_1$–$C_6$ alkyl, $C_2$–$C_4$ alkenyl, $C_2$–$C_4$ alkynyl, aryl, and aryl-$C_1$–$C_4$ alkyl.

2. A compound, salt, or ester according to claim 1, wherein:

G is selected from the group consisting of:

a) 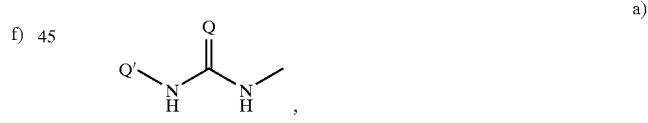

b) 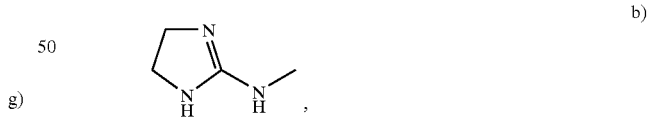

c) 

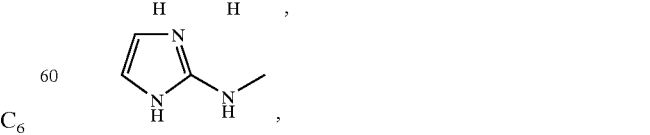

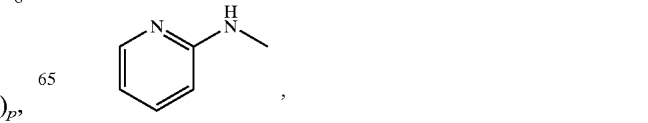

-continued

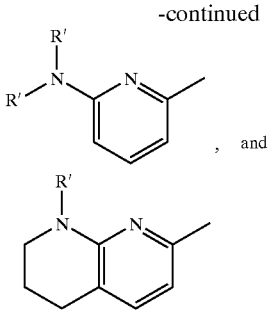
, and

B is (CH$_2$)$_q$;
q is 2, 3, or 4; and
R$_2$ is:
  phenyl optionally substituted by one to three substituents independently selected from the group consisting of halogen, CF$_3$, C$_1$–C$_4$ alkyl, hydroxy, and C$_1$–C$_4$ alkoxy;
  aralkyl; or
  pyridine optionally substituted by one to three substituents independently selected from the group consisting of halogen, CF$_3$, C$_1$–C$_4$ alkyl, hydroxy, and C$_1$–C$_4$ alkoxy.

3. A compound, salt, or ester according to claim 1, wherein:
G is selected from the group consisting of:

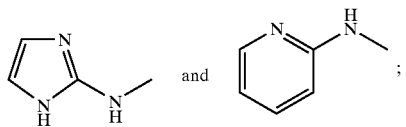

B is (CH$_2$)$_q$;
q is 2, 3, or 4;
R$_2$ is:
  a phenyl optionally substituted by one to three substituents independently selected from the aroup consisting of halogen, CF$_3$, C$_1$–C$_4$ alkyl, hydroxy, and C$_1$–C$_4$ alkoxy;
  aralkyl; or
  pyridine optionally substituted by one to three substituents independently selected from the group consisting of halogen, CF$_3$, C$_1$–C$_4$ alkyl, hydroxy, and C$_1$–C$_4$ alkoxy.

4. The compound, salt, or ester as recited in claim 1, wherein the compound is selected from the group consisting of:
(4-phenyl-6-{[3-(2-pyridinylamino)propanoyl]amino}-3,4-dihydro-2H-1,4-benzoxazin-2-yl)acetic acid;
(4-phenyl-6-{[4-(2-pyridinylamino)butanoyl]amino}-3,4-dihydro-2H-1,4-benzoxazin-2-yl)acetic acid;
(4-phenyl-6-{[5-(2-pyridinylamino)pentanoyl]amino}-3,4-dihydro-2H-1,4-benzoxazin-2-yl)acetic acid;
(4-phenyl-6-{[3-(1H-imidazol-2-ylamino)propanoyl]amino}-3,4-dihydro-2H-1,4benzoxazin-2-yl)acetic acid;
(4-phenyl-6-{[4-(1H-imidazol-2-ylamino)butanoyl]amino}-3,4-dihydro-2H-1,4-benzoxazin-2-yl)acetic acid;
(4-phenyl-6-{[5-(1H-imidazol-2-ylamino)pentanoyl]amino}-3,4-dihydro-2H-1,4-benzoxazin-2-yl)acetic acid;
(4-methyl-6-{[3-(2-pyridinylamino)propanoyl]amino}-3,4-dihydro-2H,-1,4-benzoxazin-2-yl)acetic acid;
(4-methyl-6-{[4-(2-pyridinylamino)butanoyl]amino}-3,4-dihydro-2H-1,4-benzoxazin-2yl)acetic acid;
(4-methyl-6-{[5-(2-pyridinylamino)pentanoyl]amino}-3,4-dihydro-2H,-1,4-benzoxazin-2-yl)acetic acid;
(4-methyl-6-{[3-(1H-imidazol-2-ylamino)propanoyl]amino}-3,4-dihydro-2H,-1,4-benzoxazin-2-yl)acetic acid;
(4-methyl-6-{[4-(1H-imidazol-2-ylamino)butanoyl]amino}-3,4-dihydro-2H-1,4-benzoxazin-2-yl)acetic acid; and
(4-methyl-6-{[5-(1H-imidazol-2-ylamino)pentanoyl]amino}-3,4-dihydro-2H-1,4-benzoxazin-2-yl)acetic acid.

5. The compound as recited in claim 1, wherein the compound is selected from the group consisting of:
(4-cyclopropylmethyl-6-{[3-(2-pyridinylamino)propanoyl]amino}-3,4-dihydro-2H-1,4-benzoxazin-2-yl)acetic acid;
(4-cyclopropylmethyl-6-{[4-(2-pyridinylamino)butanoyl]amino}-3,4-dihydro-2H-1,4-benzoxazin-2-yl)acetic acid;
(4-cyclopropylmethyl-6-{[5-(2-pyridinylamino)pentanoyl]amino}-3,4-dihydro-2H-1,4-benzoxazin-2-yl)acetic acid;
(4-cyclopropylmethyl-6-{[3-(1H-imidazol-2-ylamino)propanoyl]amino}-3,4-dihydro-2H-1,4-benzoxazin-2-yl)acetic acid;
(4-cyclopropylmethyl-6-{[4-(1H-imidazol-2-ylamino)butanoyl]amino}-3,4-dihydro-2H-1,4-benzoxazin-2-yl)acetic acid;
(4-cyclopropylmethyl-6-{[5-(1H-imidazol-2-ylamino)pentanoyl]amino}-3,4-dihydro- 2H-1,4-benzoxazin-2-yl)acetic acid;
(4-cyclohexylmethyl-6-{[3-(2-pyridinylamino)propanoyl]amino}-3,4-dihydro-2H-1,4-benzoxazin-2-yl)acetic acid;
(4-cyclohexylmethyl-6-{[4-(2-pyridinylamino)butanoyl]amino}-3,4-dihydro-2H-1,4-benzoxazin-2-yl)acetic acid;
(4-cyclohexylmethyl-6-{[5-(2-pyridinylamino)pentanoyl]amino}-3,4-dihydro-2H-1,4-benzoxazin-2-yl)acetic acid;
(4-cyclohexylmethyl-6-{[3-(1H-imidazol-2-ylamino)propanoyl]amino}-3,4-dihydro-2H-1,4-benzoxazin-2-yl)acetic acid;
(4-cyclohexylmethyl-6-{[4-(1H-imidazol-2-ylamino)butanoyl]amino}-3,4-dihydro-2H-1,4-benzoxazin-2-yl)acetic acid; and
(4-cyclohexylmethyl-6-{[5-(1H-imidazol-2-ylamino)pentanoyl]amino}-3,4-dihydro-2H-1,4-benzoxazin-2-yl)acetic acid;

6. The compound as recited in claim 1, wherein the compound is selected from the group consisting of:
(4-benzyl-6-{[3-(2-pyridinylamino)propanoyl]amino}-3,4-dihydro-2H-1,4-benzoxazin-2-yl)acetic acid;
(4-benzyl-6-{[4-(2-pyridinylamino)butanoyl]amino}-3,4-dihydro-2H-1,4-benzoxazin-2-yl)acetic acid;
(4-benzyl-6-{[5-(2-pyridinylamino)pentanoyl]amino}-3,4-dihydro-2H-1,4-benzoxazin-2-yl)acetic acid;
(4-benzyl-6-{[3-(1H-imidazol-2-ylamino)propanoyl]amino}-3,4-dihydro-2H-1,4-benzoxazin-2-yl)acetic acid;
(4-benzyl-6-{[4-(1H-imidazol-2-ylamino)butanoyl]amino}-3,4-dihydro-2H-1,4-benzoxazin-2-yl)acetic acid;
(4-benzyl-6-{[5-(1H-imidazol-2-ylamino)pentanoyl]amino}-3,4-dihydro-2H-1,4-benzoxazin-2-yl)acetic acid;
(4-benzoyl-6-{[3-(2-pyridinylamino)propanoyl]amino}-3,4-dihydro-2H-1,4-benzoxazin-2-yl)acetic acid;
(4-benzoyl-6-{[4-(2-pyridinylamino)butanoyl]amino}-3,4-dihydro-2H-1,4-benzoxazin-2-yl)acetic acid;
(4-benzoyl-6-{[5-(2-pyridinylamino)pentanoyl]amino}-3,4-dihydro-2H-1,4-benzoxazin-2-yl)acetic acid;
(4-benzoyl-6-{[3-(1H-imidazol-2-ylamino)propanoyl]amino}-3,4-dihydro-2H-1,4-benzoxazin-2-yl)acetic acid;
(4-benzoyl-6-{[4-(1H-imidazol-2-ylamino)butanoyl]amino}-3,4-dihydro-2H-1,4-benzoxazin-2-yl)acetic acid; and (4-benzoyl-6-{[5-(1H-imidazol-2-ylamino)pentanoyl]amino}-3,4-dihydro-2H-1,4-benzoxazin-2-yl)acetic acid.

7. The compound as recited in claim 1, wherein the compound is selected from the group consisting of:

(4-nicotinoyl-6-{[3-(2-pyridinylamino)propanoyl]amino}-3,4-dihydro-2H-1,4-benzoxazin-2-yl)acetic acid;
(4-nicotinoyl-6-{[4-(2-pyridinylamino)butanoyl]amino}-3,4-dihydro-2H-1,4-benzoxazin-2-yl)acetic acid;
(4-nicotinoyl-6-{[5-(2-pyridinylamino)pentanoyl]amino}-3,4-dihydro-2H-1,4-benzoxazin-2-yl)acetic acid;
(4-nicotinoyl-6-{[3-(1H-imidazol-2-ylamino)propanoyl]amino}-3,4-dihydro-2H-1,4-benzoxazin-2-yl)acetic acid;
(4-nicotinoyl-6-{[4-(1H-imidazol-2-ylamino)butanoyl]amino}-3,4-dihydro-2H-1,4-benzoxazin-2-yl)acetic acid;
(4-nicotinoyl-6-{[5-(1H-imidazol-2-ylamino)pentanoyl]amino}-3,4-dihydro-2H-1,4-benzoxazin-2-yl)acetic acid;
[4-phenyl-6-{[2-(2-pyridinylamino)ethylamino]carbonyl}-3,4-dihydro-2H-1,4-benzoxazin-2-yl]acetic acid;
[4-phenyl-6-{[3-(2-pyridinylamino)propylamino]carbonyl}-3,4-dihydro-2H-1,4-benzoxazin-2-yl]acetic acid;
[4-phenyl-6-{[4-(2-pyridinylamino)butylamino]carbonyl}-3,4-dihydro-2H-1,4-benzoxazin-2-yl]acetic acid;
[4-phenyl-6-{[2-(1H-imidazol-2-ylamino)ethylamino]carbonyl}-3,4-dihydro-2H-1,4-benzoxazin-2-yl]acetic acid;
[4-phenyl-6-{[3-(1H-imidazol-2-ylamino)propylamino]carbonyl}-3,4-dihydro-2H-1,4-benzoxazin-2-yl]acetic acid; and
[4-phenyl-6-{[4-(1H-imidazol-2-ylamino)butylamino]carbonyl}-3,4-dihydro-2H-1,4-benzoxazin-2-yl]acetic acid.

8. A pharmaceutical composition comprising a therapeutically effective amount of a compound of formula (I):

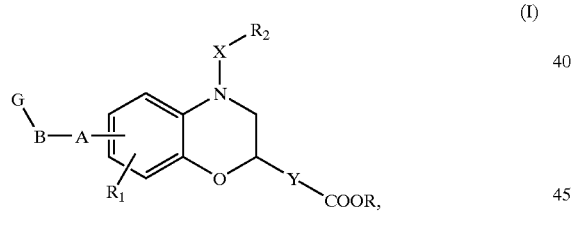

(I)

or a pharmaceutically acceptable salt or ester thereof, wherein:

G is selected from the group consisting of:

a)
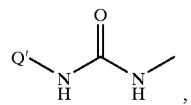

b)
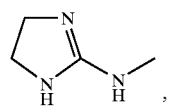

c)
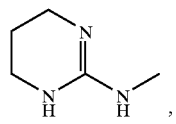

d)
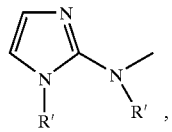

e)
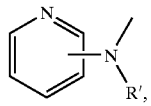

f)
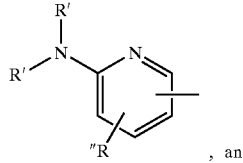

and g)
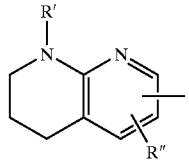

;

Q is NH or O;
Q' is selected from the group consisting of H, $C_1$–$C_6$ alkyl, phenyl, and phenyl-$C_1$–$C_4$ alkyl;
R' and R" are independently H or $C_1$–$C_4$-alkyl;
B is $C_1$–$C_4$ alkyl or $C_2$–$C_4$ alkenyl;
A is selected from the group consisting of $CH_2$, O, $S(O)_p$, NH, CON(R'''), and N(R''')CO;
R''' is hydrogen or $CH_3$;
p is zero, 1, or 2;
$R_1$ is selected from the group consisting of H, $C_1$–$C_4$ alkyl, $C_1$–$C_4$ alkoxy, OH, halogen, and $CF_3$;
X is C═O or a bond, except that X is C═O when G is:

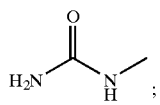

;

$R_2$ is selected from the group consisting of:
H;
$C_1$–$C_4$ alkyl;
$C_3$–$C_7$ cycloalkyl;
$C_1$–$C_4$-alkylcycloalkyl;
aryl optionally substituted by one to three substituents independently selected from the group consisting of halogen, $CF_3$, $C_1$–$C_4$ alkyl, hydroxy, and $C_1$–$C_4$ alkoxy;
aralkyl; and
a heteroaryl selected from the group consisting of pyridinyl, pyrazinyl, pyridazinyl, pyrimidinyl, thienyl, pyrrolyl, pyrazolyl, imidazolyl, oxazolyl, and isoxazolyl, wherein:
any such heteroaryl is optionally substituted by one to three substituents independently selected from the group consisting of halogen, $CF_3$, $C_1$–$C_4$ alkyl, hydroxy, and $C_1$–$C_4$ alkoxy;

Y is $(CH_2)_n$;

n is 1 or 2; and

R is selected from the group consisting of hydrogen, $C_1$–$C_6$ alkyl, $C_2$–$C_4$ alkenyl, $C_2$–$C_4$ alkynyl, aryl, and aryl-$C_1$–$C_4$ alkyl.

9. A pharmaceutical composition of claim 8, wherein:

G is selected from the group consisting of:

a) [structure]

b) [structure]

c) [structure]

[structure]

[structure]

[structure], and

[structure]

B is $(CH_2)_q$;

q is 2, 3, or 4; and $R_2$ is:
  phenyl optionally substituted by one to three substituents independently selected from the group consisting of halogen, $CF_3$, $C_1$–$C_4$ alkyl, hydroxy, and $C_1$–$C_4$ alkoxy;
  aralkyl; or
  pyridine optionally substituted by one to three substituents independently selected from the group consisting of halogen, $CF_3$, $C_1$–$C_4$ alkyl, hydroxy, and $C_1$–$C_4$ alkoxy.

10. A pharmaceutical composition of claim 8, wherein:

G is selected from the group consisting of:

[structure] and [structure];

B is $(CH_2)_q$;

q is 2, 3 or 4; and $R_2$ is:
  phenyl optionally substituted by one to three substituents independently selected from the group consisting of halogen, $CF_3$, $C_1$–$C_4$ alkyl, hydroxy, and $C_1$–$C_4$ alkoxy;
  aralkyl; or
  pyridine optionally substituted by one to three substituents independently selected from the group consisting of halogen, $CF_3$, $C_1$–$C_4$ alkyl, hydroxy, and $C_1$–$C_4$ alkoxy.

11. A pharmaceutical composition comprising a therapeutically effective amount of a compound or a pharmaceutically acceptable salt or ester thereof as recited in claim 8, wherein the compound is selected from the group consisting of:

(4-phenyl-6-{[3-(2-pyridinylamino)propanoyl]amino}-3,4-dihydro-2H-1,4-benzoxazin-2-yl)acetic acid;

(4-phenyl-6-{[4-(2-pyridinylamino)butanoyl]amino}-3,4-dihydro-2H-1,4-benzoxazin-2-yl)acetic acid;

(4-phenyl-6-{[5-(2-pyridinylamino)pentanoyl]amino}-3,4-dihydro-2H-1,4-benzoxazin-2-yl)acetic acid;

(4-phenyl-6-{[3-(1H-imidazol-2-ylamino)propanoyl]amino}-3,4-dihydro-2H-1,4-benzoxazin-2-yl)acetic acid;

(4-phenyl-6-{[4-(1H-imidazol-2-ylamino)butanoyl]amino}-3,4-dihydro-2H-1,4-benzoxazin-2-yl)acetic acid;

(4-phenyl-6-{[5-(1H-imidazol-2-ylamino)pentanoyl]amino}-3,4-dihydro-2H-1,4-benzoxazin-2-yl)acetic acid;

(4-methyl-6-{[3-(2-pyridinylamino)propanoyl]amino}-3,4-dihydro-2H-1,4-benzoxazin-2-yl)acetic acid;

(4-methyl-6-{[4-(2-pyridinylamino)butanoyl]amino}-3,4-dihydro-2H-1,4-benzoxazin-2-yl)acetic acid;

(4-methyl-6-{[5-(2-pyridinylamino)pentanoyl]amino}-3,4-dihydro-2H-1,4-benzoxazin-2-yl)acetic acid;

(4-methyl-6-{[3-(1H-imidazol-2-ylamino)propanoyl]amino}-3,4-dihydro-2H-1,4-benzoxazin-2-yl)acetic acid;

(4-methyl-6-{[4-(1H-imidazol-2-ylamino)butanoyl]amino}-3,4-dihydro-2H-1,4-benzoxazin-2-yl)acetic acid; and (4-methyl-6-{[5-(1H-imidazol-2-ylamino)pentanoyl]amino}-3,4-dihydro-2H-1,4-benzoxazin-2-yl)acetic acid.

12. A pharmaceutical composition comprising a therapeutically effective amount of a compound or a pharmaceutically acceptable salt or ester thereof as recited in claim 8, wherein the compound is selected from the group consisting of:

(4-cyclopropylmethyl-6-{[3-(2-pyridinylamino)propanoyl]amino}-3,4-dihydro-2H-1,4-benzoxazin-2-yl)acetic acid;

(4-cyclopropylmethyl-6-{[4-(2-pyridinylamino)butanoyl]amino}-3,4-dihydro-2H-1,4-benzoxazin-2-yl)acetic acid;

(4-cyclopropylmethyl-6-{[5-(2-pyridinylamino)pentanoyl]amino}-3,4-dihydro-2H-1,4-benzoxazin-2-yl)acetic acid;

(4-cyclopropylmethyl-6-{[3-(1H-imidazol-2-ylamino)propanoyl]amino}-3,4-dihydro-2H-1,4-benzoxazin-2-yl)acetic acid;

(4-cyclopropylmethyl-6-{[4-(1H-imidazol-2-ylamino)butanoyl]amino}-3,4-dihydro-2H-1,4-benzoxazin-2-yl)acetic acid;

(4-cyclopropylmethyl-6-{[5-(1H-imidazol-2-ylamino)pentanoyl]amino}-3,4-dihydro-2H-1,4-benzoxazin-2-yl)acetic acid;

(4-cyclohexylmethyl-6-{[3-(2-pyridinylamino)propanoyl]amino}-3,4-dihydro-2H-1,4-benzoxazin-2-yl)acetic acid;

(4-cyclohexylmethyl-6-{[4-(2-pyridinylamino)butanoyl]amino}-3,4-dihydro-2H-1,4-benzoxazin-2-yl)acetic acid;

(4-cyclohexylmethyl-6-{[5-(2-pyridinylamnino)pentanoyl]amino}-3,4-dihydro-2H-1,4-benzoxazin-2-yl)acetic acid;

(4-cyclohexylmethyl-6-{[3-(1H-imidazol-2-ylamino)propanoyl]amino}-3,4-dihydro-2H-1,4-benzoxazin-2-yl)acetic acid;
(4-cyclohexylmethyl-6-{[4-(1H-imidazol-2-ylamino)butanoyl]amino}-3,4-dihydro-2H-1,4-benzoxazin-2-yl)acetic acid; and
(4-cyclohexylmethyl-6-{[5-(1H-imidazol-2-ylamino)pentanoyl]amino}-3,4-dihydro-2H-1,4-benzoxazin-2-yl)acetic acid.

13. A pharmaceutical composition comprising a therapeutically effective amount of a compound or a pharmaceutically acceptable salt or ester thereof as recited in claim 8, wherein the compound is selected from the group consisting of:
(4-benzyl-6-{[3-(2-pyridinylamino)propanoyl]amino}-3,4-dihydro-2H-1,4-benzoxazin-2-yl)acetic acid;
(4-benzyl-6-{[4-(2-pyridinylamino)butanoyl]amino}-3,4-dihydro-2H-1,4-benzoxazin-2-yl)acetic acid;
(4-benzyl-6-{[5-(2-pyridinylamino)pentanoyl]amino}-3,4-dihydro-2H-1,4-benzoxazin-2-yl)acetic acid;
(4-benzyl-6-{[3-(1H-imidazol-2-ylamino)propanoyl]amino}-3,4-dihydro-2H-1,4-benzoxazin-2-yl)acetic acid;
(4-benzyl-6-{[4-(1H-imidazol-2-ylamino)butanoyl]amino}-3,4-dihydro-2H-1,4-benzoxazin-2-yl)acetic acid;
(4-benzyl-6-{[5-(1H-imidazol-2-ylamino)pentanoyl]amino}-3,4-dihydro-2H-1,4-benzoxazin-2-yl)acetic acid;
(4-benzoyl-6-{[3-(2-pyridinylamino)propanoyl]amino}-3,4-dihydro-2H-1,4-benzoxazin-2-yl)acetic acid;
(4-benzoyl-6-{[4-(2-pyridinylamino)butanoyl]amino}-3,4-dihydro-2H-1,4-benzoxazin-2-yl)acetic acid;
(4-benzoyl-6-{[5-(2-pyridinylamino)pentanoyl]amino}-3,4-dihydro-2H-1,4-benzoxazin-2-yl)acetic acid;
(4-benzoyl-6-{[3-(1H-imidazol-2-ylamino)propanoyl]amino}-3,4-dihydro-2H-1,4-benzoxazin-2-yl)acetic acid;
(4-benzoyl-6-{[4-(1H-imidazol-2-ylamino)butanoyl]amino}-3,4-dihydro-2H-1,4-benzoxazin-2-yl)acetic acid; and
(4-benzoyl-6-{[5-(1H-imidazol-2-ylamino)pentanoyl]amino}-3,4-dihydro-2H-1,4-benzoxazin-2-yl)acetic acid.

14. A pharmaceutical composition comprising a therapeutically effective amount of a compound or a pharmaceutically acceptable salt or ester thereof as recited in claim 8, wherein the compound is selected from the group consisting of:
(4-nicotinoyl-6-{[3-(2-pyridinylamino)propanoyl]amino}-3,4-dihydro-2H-1,4-benzoxazin-2-yl)acetic acid;
(4-nicotinoyl-6-{[4-(2-pyridinylamino)butanoyl]amino}-3,4-dihydro-2H-1,4-benzoxazin-2-yl)acetic acid;
(4-nicotinoyl-6-{[5-(2-pyridinylamino)pentanoyl]amino}-3,4-dihydro-2H-1,4-benzoxazin-2-yl)acetic acid;
(4-nicotinoyl-6-{[3-(1H-imidazol-2-ylamino)propanoyl]amino}-3,4-dihydro-2H-1,4-benzoxazin-2-yl)acetic acid;
(4-nicotinoyl-6-{[4-(1H-imidazol-2-ylamino)butanoyl]amino}-3,4-dihydro-2H-1,4-benzoxazin-2-yl)acetic acid;
(4-nicotinoyl-6-{[5-(1H-imidazol-2-ylamino)pentanoyl]amino}-3,4-dihydro-2H-1,4-benzoxazin-2-yl)acetic acid;
[4-phenyl-6-{[2-(2-pyridinylamino)ethylamino]carbonyl}-3,4-dihydro-2H-1,4-benzoxazin-2-yl]acetic acid;
[4-phenyl-6-{[3-(2-pyridinylamino)propylamino]carbonyl}-3,4-dihydro-2H-1,4-benzoxazin-2-yl]acetic acid;
[4-phenyl-6-{[4-(2-pyridinylamino)butylamino]carbonyl}-3,4-dihydro-2H-1,4-benzoxazin-2-yl]acetic acid;
[4-phenyl-6-{[2-(1H-imidazol-2-ylamino)ethylamino]carbonyl}-3,4-dihydro-2H-1,4-benzoxazin-2-yl]acetic acid;
[4-phenyl-6-{[3-(1H-imidazol-2-ylamino)propylamino]carbonyl}-3,4-dihydro-2H-1,4-benzoxazin-2-yl]acetic acid; and
[4-phenyl-6-{[4-(1H-imidazol-2-ylamino)butylamino]carbonyl}-3,4-dihydro-2H-1,4-benzoxazin-2-yl]acetic acid.

15. A combination pack containing a compound of formula (I) as defined in claim 1 or a pharmaceutically acceptable salt thereof, and an effective antineoplastic amount of additional antitumor agent as a combined preparation for simultaneous, separate, or sequential use in anti-cancer therapy.

16. The combination pack according to claim 15, wherein the additional antitumor agent is selected from the group consisting of an antineoplastic topoisomerase II inhibitor, an antineoplastic antimicrotubule agent, an antineoplastic alkylating agent, an antineoplastic antimetabolite, and an antineoplastic topoisomerase I inhibitor.

17. A method for treating a mammal having a condition treatable by Inhlbiting $\alpha_v\beta_3$ integrin, wherein:
the method comprises administering to said mammal an effective $\alpha_v\beta_3$ inhibiting amount of a compound of formula (I) (or a pharmaceutically acceptable salt or ester thereof):

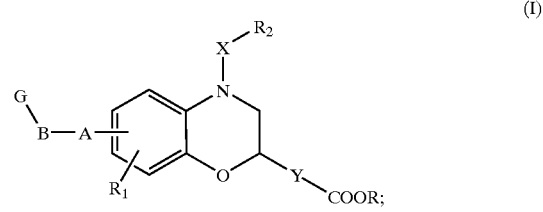

(I)

G is selected from the group consisting of:

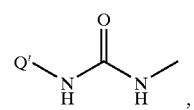

a)

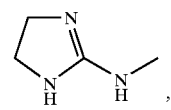

b)

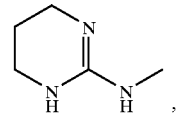

c)

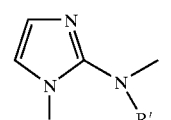

d)

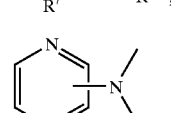

e)

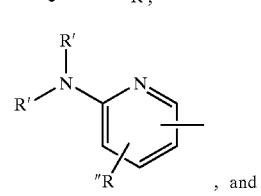

f)

, and

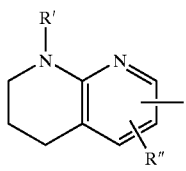

Q is NH or O;

Q' is selected from the group consisting of H, $C_1$–$C_6$ alkyl, phenyl, and phenyl-$C_1$–$C_4$-alkyl;

R' and R" are independently H or $C_1$–$C_4$-alkyl;

B is $C_1$–$C_4$ alkyl or $C_2$–$C_4$ alkenyl;

A is selected from the group consisting of $CH_2$, O, $S(O)_p$ NH, CON(R'"), and N(R'")CO;

p is zero, 1, or 2;

R'" is hydrogen or $CH_3$;

$R_1$ is selected from the group consisting of H, $C_1$–$C_4$ alkyl, $C_1$–$C_4$ alkoxy, OH, halogen, and $CF_3$;

X is C= and a bond, except that X is C=O when G is:

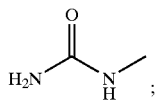

$R_2$ is selected from the group consisting of:
  H;
  $C_1$–$C_4$ alkyl;
  $C_3$–$C_7$ cycloalkyl;
  $C_1$–$C_4$-alkylcycloalkyl;
  aryl optionally substituted by one to three substituents independently selected from the group consisting of halogen, $CF_3$, $C_1$–$C_4$ alkyl, hydroxy, and $C_1$–$C_4$ alkoxy;
  aralkyl; and
  a heteroaryl selected from the group consisting of pyridinyl, pyrazinyl, pyridazinyl, primidinyl, thienyl, pyrrolyl, pyrazolyl, imidazolyl, oxazolyl, and isoxazolyl, wherein:
    any such heteroaryl is optionally substituted by one to three substituents independently selected from the group consisting of halogen, $CF_3$, $C_1$–$C_4$ alkyl, hydroxy, and $C_1$–$C_4$ alkoxy;

Y is $(CH_2)_n$;

n is 1 or 2; and

R is selected from the group consisting of hydrogen, $C_1$–$C_6$ alkyl, $C_2$–$C_4$ alkenyl, $C_2$–$C_4$ alkynyl, aryl, and aryl-$C_1$–$C_4$ alkyl.

18. The method of claim 17, wherein;

G is selected from the group consisting of:

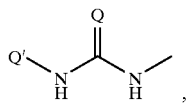

a)

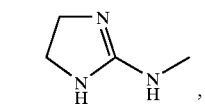

b)

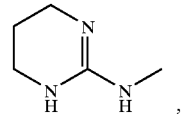

c)

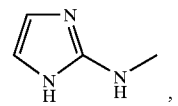

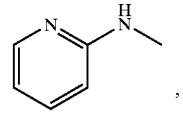

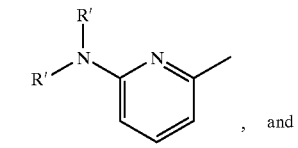

, and

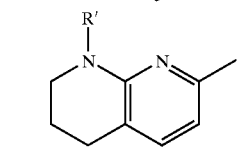

B is $(CH_2)_q$;

q is 2, 3, or 4; and $R_2$ is:
  phenyl optionally substituted by one to three substituents independently selected from the group consisting of halogen, $CF_3$, $C_1$–$C_4$ alkyl, hydroxy, and $C_1$–$C_4$ alkoxy;
  aralkyl; or
  pyridine optionally substituted by one to three substituents independently selected from the group consisting of halogen, $CF_3$, $C_1$–$C_4$ alkyl, hydroxy, and $C_1$–$C_4$ alkoxy.

19. The method of claim 17, wherein:

G is selected from the group consisting of:

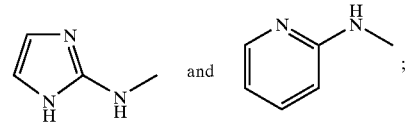

B is $(CH_2)_q$;

q is 2, 3 or 4; and $R_2$ is:
  phenyl optionally substituted by one to three substituents independently selected from the group consisting of halogen, $CF_3$, $C_1$–$C_4$ alkyl, hydroxy, and $C_1$–$C_4$ alkoxy;
  aralkyl; or
  pyridine optionally substituted by one to three substituents independently selected from the group consisting of halogen, $CF_3$, $C_1$–$C_4$ alkyl, hydroxy, and $C_1$–$C_4$ alkoxy.

20. The method according to claim 17, wherein the compound is selected from the group consisting of:

(4-phenyl-6-{[3-(2-pyridinylamino)propanoyl]amino}-3,4-dihydro-2H-1,4-benzoxazin-2-yl)acetic acid;
(4-phenyl-6-{[4-(2-pyridinylamino)butanoyl]amino}-3,4-dihydro-2H-1,4-benzoxazin-2-yl)acetic acid;
(4-phenyl-6-{[5-(2-pyridinylamino)pentanoyl]amino}-3,4-dihydro-2H-1,4-benzoxazin-2-yl)acetic acid;
(4-phenyl-6-{[3-(1H-imidazol-2-ylamino)propanoyl]amino}-3,4-dihydro-2H-1,4-benzoxazin-2-yl)acetic acid;
(4-phenyl-6-{[4-(1H-imidazol-2-ylamino)butanoyl]amino}-3,4-dihydro-2H-1,4-benzoxazin-2-yl)acetic acid;
(4-phenyl-6-{[5-(1H-imidazol-2-ylamino)pentanoyl]amino}-3,4-dihydro-2H-1,4-benzoxazin-2-yl)acetic acid;
(4-methyl-6-{[3-(2-pyridinylamino)propanoyl]amino}-3,4-dihydro-2H-1,4-benzoxazin-2-yl)acetic acid;
(4-methyl-6-{[4-(2-pyridinylamino)butanoyl]amino}-3,4-dihydro-2H-1,4-benzoxazin-2-yl)acetic acid;
(4-methyl-6-{[5-(2-pyridinylamino)pentanoyl]amino}-3,4-dihydro-2H-1,4-benzoxazin-2-yl)acetic acid;
(4-methyl-6-{[3-(1H-imidazol-2-ylamino)propanoyl]amino}-3,4-dihydro-2H-1,4-benzoxazin-2-yl)acetic acid;
(4-methyl-6-{[4-(1H-imidazol-2-ylamino)butanoyl]amino}-3,4-dihydro-2H-1,4-benzoxazin-2-yl)acetic acid; and
(4-methyl -6-{[5-(1H-imidazol-2-ylamino)pentanoyl]amino}-3,4-dihydro-2H-1,4-benzoxazin-2-yl)acetic acid.

21. The method according to claim 17, wherein the condition treated is bone resorption, osteoporosis, humoral hypercalcemia of malignancy, Paget's disease, tumor metastasis, neoplasia (solid tumor growth), angiogenesis, diabetic retinopathy, arthritis, psoriasis, periodontal disease, or smooth muscle cell migration.

22. The method according to claim 20, wherein the condition treated is bone resorption, osteoporosis, humoral hypercalcemia of malignancy, Paget's disease, tumor metastasis, neoplasia (solid tumor growth), angiogenesis, diabetic retinopathy, arthritis, psoriasis, periodontal disease, or smooth muscle cell migration.

23. A combined method of treatment of cancer or of controlling the growth of a neoplasm in a mammal suffering from cancer, said method comprising administering simultaneous, separately, or sequentially the following agents in amounts and close enough together in time sufficient to roduce a therapeutically useful effect:
  1) a compound of formula (I) as defined in claim 1 or a pharmaceutically acceptable salt thereof; and
  2) an additional antitumor agent.

24. The method according to claim 33, wherein the additional antitumor agent is selected from the group consisting of an antineoplastic topoisomerase II inhibitor, an antineoplastic antimicrotubule agent, an antineoplastic alkylating agent, an antineoplastic antimetabolite and an antineoplastic topoisomerase I inhibitor.

25. The method according to claim 17, wherein the compound is selected from the group consisting of:
(4-cyclopropylmethyl-6-{[3-(2-pyridinylamino)propanoyl]amino}-3,4-dihydro-2H-1,4-benzoxazin-2-yl)acetic acid;
(4-cyclopropylmethyl-6-{[4-(2-pyridinylamino)butanoyl]amino}-3,4-dihydro-2H-1,4-benzoxazin-2-yl)acetic acid;
(4-cyclopropylmethyl-6-{[5-(2-pyridinylamino)pentanoyl]amino}-3,4-dihydro-2H-1,4-benzoxazin-2-yl)acetic acid;
(4-cyclopropylmethyl-6-{[3-(1H-imidazol-2-ylamino)propanoyl]amino}-3,4-dihydro-2H-1,4-benzoxazin-2-yl)acetic acid;
(4-cyclopropylmethyl-6-{[4-(1H-imidazol-2-ylamino)butanoyl]amino}-3,4-dihydro-2H-1,4-benzoxazin-2-yl)acetic acid;
(4-cyclopropylmethyl-6-{[5-(1H-imidazol-2-ylamino)pentanoyl]amino}-3,4-dihydro-2H-1,4-benzoxazin-2-yl)acetic acid;
(4-cyclohexylmethyl-6-{[3-(2-pyridinylamino)propanoyl]amino}-3,4-dihydro-2H-1,4-benzoxazin-2-yl)acetic acid;
(4-cyclohexylmethyl-6-{[4-(2-pyridinylamino)butanoyl]amino}-3,4-dihydro-2H-1,4-benzoxazin-2-yl)acetic acid;
(4-cyclohexylmethyl-6-{[5-(2-pyridinylamino)pentanoyl]amino}-3,4-dihydro-2H-1,4-benzoxazin-2-yl)acetic acid;
(4-cyclohexylmethyl-6-{[3-(1H-imidazol-2-ylamino)propanoyl]amino}-3,4-dihydro-2H-1,4-benzoxazin-2-yl)acetic acid;
(4-cyclohexylmethyl-6-{[4-(1H-imidazol-2-ylamino)butanoyl]amino}-3,4-dihydro-2H-1,4-benzoxazin-2-yl)acetic acid; and
(4-cyclohexylmethyl-6-{[5-(1H-imidazol-2-ylamino)pentanoyl]amino}-3,4-dihydro-2H-1,4-benzoxazin-2-yl)acetic acid.

26. The method according to claim 17, wherein the compound is selected from the group consisting of:
(4-benzyl-6-{[3-(2-pyridinylamino)propanoyl]amino}-3,4-dihydro-2H-1,4-benzoxazin-2-yl)acetic acid;
(4-benzyl-6-{[4-(2-pyridinylamino)butanoyl]amino}-3,4-dihydro-2H-1,4-benzoxazin-2-yl)acetic acid;
(4-benzyl-6-{[5-(2-pyridinylamino)pentanoyl]amino}-3,4-dihydro-2H-1,4-benzoxazin-2-yl)acetic acid;
(4-benzyl-6-{[3-(1H-imidazol-2-ylamino)propanoyl]amino}-3,4-dihydro-2H-1,4-benzoxazin-2-yl)acetic acid;
(4-benzyl-6-{[4-(1H-imidazol-2-ylamino)butanoyl]amino}-3,4-dihydro-2H-1,4-benzoxazin-2-yl)acetic acid;
(4-benzyl-6-{[5-(1H-imidazol-2-ylamino)pentanoyl]amino}-3,4-dihydro-2H-1,4-benzoxazin-2-yl)acetic acid;
(4-benzoyl-6-{[3-(2-pyridinylamino)propanoyl]amino}-3,4-dihydro-2H-1,4-benzoxazin-2-yl)acetic acid;
(4-benzoyl-6-{[4-(2-pyridinylamino)butanoyl]amino}-3,4-dihydro-2H-1,4-benzoxazin-2-yl)acetic acid;
(4-benzoyl-6-{[5-(2-pyridinylamino)pentanoyl]amino}-3,4-dihydro-2H-1,4-benzoxazin-2-yl)acetic acid;
(4-benzoyl-6-{[3-(1H-imidazol-2-ylamino)propanoyl]amino}-3,4-dihydro-2H-1,4-benzoxazin-2-yl)acetic acid;
(4-benzoyl-6-{[4-(1H-imidazol-2-ylamino)butanoyl]amino}-3,4-dihydro-2H-1,4-benzoxazin-2-yl)acetic acid; and
(4-benzoyl-6-{[5-(1H-imidazol-2-ylamino)pentanoyl]amino}-3,4-dihydro-2H-1,4-benzoxazin-2-yl)acetic acid.

27. The method according to claim 17, wherein the compound is selected from the group consisting of:
(4-nicotinoyl-6-{[3-(2-pyridinylamino)propanoyl]amino}-3,4-dihydro-2H-1,4-benzoxazin-2-yl)acetic acid;
(4-nicotinoyl-6-{[4-(2-pyridinylamino)butanoyl]amino}-3,4-dihydro-2H-1,4-benzoxazin-2-yl)acetic acid;
(4-nicotinoyl-6-{[5-(2-pyridinylamino)pentanoyl]amino}-3,4-dihydro-2H-1,4-benzoxazin-2-yl)acetic acid;
(4-nicotinoyl-6-{[3-(1H-imidazol-2-ylamino)propanoyl]amino}-3,4-dihydro-2H-1,4-benzoxazin-2-yl)acetic acid;
(4-nicotinoyl-6-{[4-(1H-imidazol-2-ylamino)butanoyl]amino}-3,4-dihydro-2H-1,4-benzoxazin-2-yl)acetic acid;
(4-nicotinoyl-6-{[5-(1H-imidazol-2-ylamino)pentanoyl]amino}-3,4-dihydro-2H-1,4-benzoxazin-2-yl)acetic acid;
[4-phenyl-6-{[2-(2-pyridinylamino)ethylamino]carbonyl}-3,4-dihydro-2H-1,4-benzoxazin-2-yl]acetic acid;

[4-phenyl-6-{[3-(2-pyridinylamino)propylamino]carbonyl}-3,4-dihydro-2H-1,4-benzoxazin-2-yl]acetic acid;

[4-phenyl-6-{[4-(2-pyridinylamino)butylamino]carbonyl}-3,4-dihydro-2H-1,4-benzoxazin-2-yl]acetic acid;

[4-phenyl-6-{[2-(1H-imidazol-2-ylamino)ethylamino]carbonyl}-3,4-dihydro-2H-1,4-benzoxazin-2-yl]acetic acid;

[4-phenyl-6-{[3-(1H-imidazol-2-ylamino)propylamino]carbonyl}-3,4-dihydro-2H-1,4-benzoxazin-2-yl]acetic acid; and

[4-phenyl-6-{[4-(1H-imidazol-2-ylamino)butylamino]carbonyl}-3,4-dihydro-2H-1,4-benzoxazin-2-yl]acetic acid.

* * * * *